(12) United States Patent
Kurasawa et al.

(10) Patent No.: US 11,054,954 B2
(45) Date of Patent: Jul. 6, 2021

(54) FINGERPRINT DETECTION DEVICE AND DISPLAY DEVICE

(71) Applicant: Japan Display Inc., Tokyo (JP)

(72) Inventors: Hayato Kurasawa, Tokyo (JP); Yoshitaka Ozeki, Tokyo (JP); Toshinori Uehara, Tokyo (JP); Yuji Suzuki, Tokyo (JP)

(73) Assignee: Japan Display Inc., Tokyo (JP)

( * ) Notice: Subject to any disclaimer, the term of this patent is extended or adjusted under 35 U.S.C. 154(b) by 0 days.

(21) Appl. No.: 16/828,296

(22) Filed: Mar. 24, 2020

(65) Prior Publication Data
US 2020/0226343 A1 Jul. 16, 2020

Related U.S. Application Data

(63) Continuation of application No. PCT/JP2018/036258, filed on Sep. 28, 2018.

(30) Foreign Application Priority Data

Sep. 29, 2017 (JP) .............................. JP2017-191845

(51) Int. Cl.
*G06F 3/044* (2006.01)
*G06F 3/042* (2006.01)
*G06K 9/00* (2006.01)

(52) U.S. Cl.
CPC .......... *G06F 3/0445* (2019.05); *G06F 3/0421* (2013.01); *G06F 3/0446* (2019.05);
(Continued)

(58) Field of Classification Search
CPC .... G06F 3/0445; G06F 3/0446; G06F 3/0448; G06F 3/0421; G06F 2203/04107; G06F 2203/04112; G06K 9/0004
See application file for complete search history.

(56) References Cited

U.S. PATENT DOCUMENTS 6,401,551 B1    6/2002  Kawahara et al.
2001/0047687 A1*  12/2001  Abe .................... G01C 19/5607
                                                    73/504.16
(Continued)

FOREIGN PATENT DOCUMENTS

JP    2001-052148    6/2002
JP    2011-180854    9/2011
(Continued)

OTHER PUBLICATIONS

International Search Report issued in International Patent Application No. PCT/JP2018/036258, dated Oct. 30, 2018, and English translation of same. 6 pages.

*Primary Examiner* — Antonio Xavier
(74) *Attorney, Agent, or Firm* — K&L Gates

(57) ABSTRACT

According to an aspect, a fingerprint detection device includes: a substrate; a plurality of drive electrodes provided on one surface side of the substrate and arranged in a first direction; a plurality of detection electrodes provided on the one surface side and arranged in a second direction intersecting the first direction; and an insulating layer provided in a normal direction of the substrate between each of the drive electrodes and the corresponding detection electrodes. The detection electrodes intersect the drive electrodes in the normal direction of the substrate. The detection electrodes include: a first metallic layer; and a second metallic layer positioned closer to the one surface than the first metallic layer to the one surface. The first metallic layer has a reflectance of visible light lower than that of the second metallic layer.

16 Claims, 30 Drawing Sheets

(52) U.S. Cl.
CPC ......... *G06F 3/0448* (2019.05); *G06K 9/0004* (2013.01); *G06F 2203/04107* (2013.01); *G06F 2203/04112* (2013.01)

(56) References Cited

U.S. PATENT DOCUMENTS

| | | |
|---|---|---|
| 2010/0152794 A1 | 6/2010 | Radivojevic et al. |
| 2011/0216033 A1 | 9/2011 | Mamba et al. |
| 2012/0241408 A1* | 9/2012 | Misaki .................... B32B 15/04 216/20 |
| 2012/0247207 A1* | 10/2012 | Takaoka ............. G01C 19/5769 73/504.12 |
| 2012/0249454 A1* | 10/2012 | Teraguchi ............. G06F 3/0445 345/173 |
| 2013/0050107 A1 | 2/2013 | Xie et al. |
| 2014/0253826 A1* | 9/2014 | He ........................ G06F 3/0443 349/12 |
| 2014/0333855 A1 | 11/2014 | Park et al. |
| 2015/0277485 A1* | 10/2015 | Kosugi .................. G06F 3/0445 345/174 |
| 2015/0309358 A1* | 10/2015 | Nomura .............. G02F 1/13439 349/42 |
| 2015/0356911 A1 | 12/2015 | Mizihashi et al. |
| 2017/0083137 A1 | 3/2017 | Kurasawa et al. |
| 2017/0123566 A1* | 5/2017 | Noguchi ................ G06F 3/0445 |
| 2019/0004656 A1 | 1/2019 | Hoka et al. |
| 2019/0049597 A1* | 2/2019 | Tian ........................ G01T 1/208 |

FOREIGN PATENT DOCUMENTS

| | | |
|---|---|---|
| JP | 2012-511360 | 5/2012 |
| JP | 2014-529128 | 10/2014 |
| JP | 2014-219987 | 11/2014 |
| JP | 2015-230607 | 12/2015 |
| JP | 2017-059147 | 3/2017 |
| WO | WO2017/150197 | 9/2017 |

* cited by examiner

FINGERPRINT DETECTION DEVICE AND DISPLAY DEVICE

CROSS-REFERENCE TO RELATED APPLICATIONS

This application is a continuation of International Application No. PCT/JP2018/036258, filed on Sep. 28, 2018, which claims priority to Japanese Application No. 2017-191845, filed on Sep. 29, 2017. The contents of these applications are incorporated herein by reference in their entirety.

BACKGROUND

1. Technical Field

The present disclosure relates to a fingerprint detection device and a display device.

2. Description of the Related Art

A display device including a liquid crystal panel or the like may be provided with a fingerprint sensor in some cases. A fingerprint sensor of Japanese Patent Application Laid-open Publication No. 2001-52148 detects a capacitance change corresponding to a recess or protrusion of a fingerprint to detect the shape of a fingerprint of a finger being in contact with the display device. A detection result of the fingerprint sensor is used for personal authentication, for example. The surface of the fingerprint sensor is provided with a cover glass. When a finger is in contact with or proximity to the surface of the cover glass, the fingerprint sensor can detect its fingerprint.

Electrodes in a fingerprint detection region reflects light entering from the cover glass side. When the fingerprint detection region is arranged at a position overlapping with a display region of the display device, the reflection of light by the electrodes in the fingerprint detection region may lead to unintended patterns (e.g., moire and a light reflecting pattern) that can be visually recognized.

For the foregoing reasons, there is a need for a fingerprint detection device and a display device that can reduce the reflection of light.

SUMMARY

According to an aspect, a fingerprint detection device includes: a substrate; a plurality of drive electrodes provided on one surface side of the substrate and arranged in a first direction; a plurality of detection electrodes provided on the one surface side and arranged in a second direction intersecting the first direction; and an insulating layer provided in a normal direction of the substrate between each of the drive electrodes and the corresponding detection electrodes. The detection electrodes intersect the drive electrodes in the normal direction of the substrate. The detection electrodes include: a first metallic layer; and a second metallic layer positioned closer to the one surface than the first metallic layer to the one surface. The first metallic layer has a reflectance of visible light lower than that of the second metallic layer.

According to another aspect, a display device includes: a display panel; and a fingerprint detection device arranged facing the display panel, the finger print detection device including: a substrate; a plurality of drive electrodes provided on one surface side of the substrate and arranged in a first direction; a plurality of detection electrodes provided on the one surface side and arranged in a second direction intersecting the first direction; and an insulating layer provided in a normal direction of the substrate between each of the drive electrodes and the corresponding detection electrodes. The detection electrodes intersect the drive electrodes in the normal direction of the substrate. Each of the detection electrodes includes: a first metallic layer; and a second metallic layer positioned closer to the one surface than the first metallic layer to the one surface. The first metallic layer has a reflectance of visible light lower than that of the second metallic layer.

DETAILED DESCRIPTION

Figure 1:
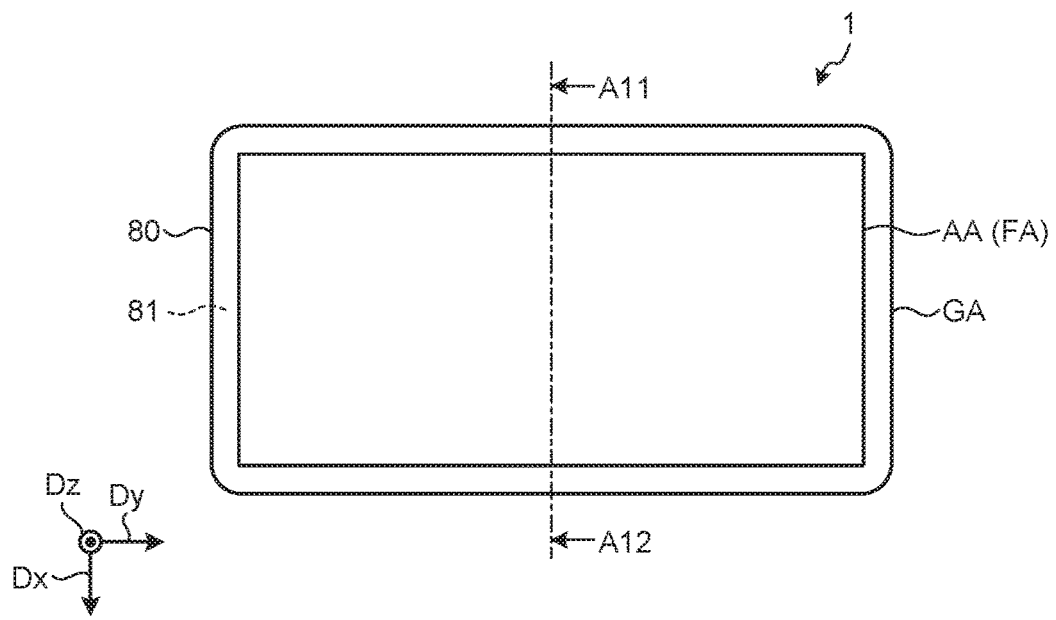
FIG. 1 is a plan view illustrating a display device according to a first embodiment.

Exemplary aspects (embodiments) according to the present disclosure are described below in greater detail with reference to the accompanying drawings. The contents described in the embodiments are not intended to limit the present disclosure. Components described below include components easily conceivable by those skilled in the art and components substantially identical therewith. Furthermore, the components described below can be appropriately combined. The disclosure is given by way of example only, and various changes made without departing from the spirit of the disclosure and easily conceivable by those skilled in the art are naturally included in the scope of the disclosure. The drawings may possibly illustrate the width, the thickness, the shape, and the like of each unit more schematically than the actual aspect to simplify the explanation. These elements, however, are given by way of example only and are not intended to limit interpretation of the present disclosure. In the specification and the drawings, components similar to those previously described with reference to a preceding drawing are denoted by like reference numerals, and detailed explanation thereof will be appropriately omitted. In this disclosure, when an element A is described as being "on" another element B, the element A can be directly on the other element B, or there can be one or more elements between the element A and the other element B.

First Embodiment

Figure 2:
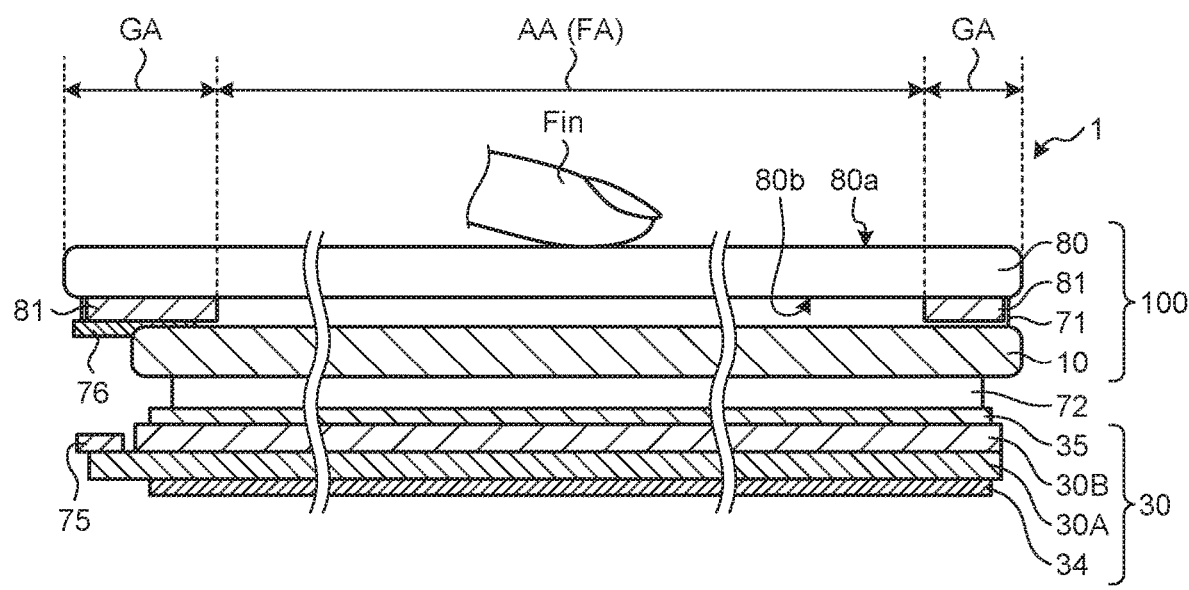
FIG. 2 is a sectional view obtained by cutting the display device illustrated in FIG. 1 along the A11-A12 line.

FIG. 1 is a plan view illustrating a display device according to a first embodiment. FIG. 2 is a sectional view obtained by cutting the display device illustrated in FIG. 1 along the A11-A12 line. The display device 1 illustrated in FIG. 1 is a display device equipped with a fingerprint detection function and includes: a display region AA for displaying an image; a fingerprint detection region FA; and a frame region GA provided outside the display region AA and the fingerprint detection region FA. The fingerprint detection region FA is a region for detecting a recess or protrusion on the surface of a finger or the like being in contact with or in proximity to a cover member 80. In the display device 1 of the present embodiment, the display region AA and the fingerprint detection region FA match with each other or substantially match with each other, thereby enabling detection of a fingerprint across the entire display region AA. The shape of the display region AA and that of the fingerprint detection region FA are rectangular, for example.

As illustrated in FIG. 2, the display device 1 of the present embodiment includes a display panel 30 and a fingerprint detection device 100. The fingerprint detection device 100 has a fingerprint sensor 10 and the cover member 80. The cover member 80 is a plate-shaped member having a first surface 80a and a second surface 80b on the side opposite of the first surface 80a. The first surface 80a of the cover member 80 is a detection surface for detecting the recess or protrusion on the surface of the finger or the like being in contact therewith or in proximity thereto, and is also a display surface for allowing an observer to visually recognize an image on the display panel 30. The fingerprint sensor 10 and the display panel 30 are provided on the second surface 80b side of the cover member 80. The cover member 80 is a member for protecting the fingerprint sensor 10 and the display panel 30 and covers the fingerprint sensor 10 and the display panel 30. The cover member 80 is a glass substrate or a resin substrate, for example.

The shapes of the cover member 80, the fingerprint sensor 10, and the display panel 30 are not limited to be rectangular in a plan view, and may be circular, oval, or an odd shape with part of these outer shape lacked. The shape of the cover member 80 is not limited to be plate-shaped. When the display region AA and the fingerprint detection region FA each have a curved surface or the frame region GA has a curved surface curving toward the display panel 30, for example, the cover member 80 may have a curved surface. In this case, the display device is a curved surface display having a fingerprint detection function and can detect a fingerprint also on the curved surface of the curved surface display. A "plan view" indicates a case when viewed from a direction perpendicular to one surface 101a of a substrate 101 illustrated in FIG. 3 described below. The direction perpendicular to the one surface 101a is a "normal direction Dz of the substrate 101".

As illustrated in FIG. 1 and FIG. 2, in the frame region GA, a decorative layer 81 is provided on the second surface 80b of the cover member 80. The decorative layer 81 is a coloring layer, light transmittance of which is lower than that of the cover member 80. The decorative layer 81 can prevent wiring, circuits, and the like provided superimposed on the frame region GA from being visually recognized by the observer. In the example illustrated in FIG. 2, the decorative layer 81 is provided on the second surface 80b, but it may be provided on the first surface 80a. The decorative layer 81 is not limited to be a single layer and may have a multilayered configuration.

The fingerprint sensor 10 is a detector for detecting a recess or protrusion on the surface of a finger Fin or the like being in contact with or in proximity to the first surface 80a of the cover member 80. As illustrated in FIG. 2, the fingerprint sensor 10 is provided between the cover member 80 and the display panel 30. When viewed from a direction perpendicular to the first surface 80a (a normal direction), the fingerprint sensor 10 overlaps with the fingerprint detection region FA and part of the frame region GA. A flexible substrate 76 is connected to the fingerprint sensor 10 in the frame region GA. An integrated circuit (IC) for detection (not illustrated) for controlling detection operations of the fingerprint sensor 10 is mounted on the flexible substrate 76.

One surface of the fingerprint sensor 10 is stuck to the second surface 80b of the cover member 80 with an adhesive layer 71, whereas the other surface thereof is stuck to a polarizing plate 35 of the display panel 30 with an adhesive layer 72. Each of the adhesive layer 71 and the adhesive layer 72 is an adhesive or a resin having translucency, and allows visible light to pass therethrough.

The display panel 30 includes: a pixel substrate 30A; a counter substrate 30B; a polarizing plate 34 provided below the pixel substrate 30A; and the polarizing plate 35 provided above the counter substrate 30B. An IC for display (not illustrated) for controlling a display operation of the display panel 30 is connected to the pixel substrate 30A via a flexible substrate 75. In the present embodiment, the display panel 30 is a liquid crystal panel in which a liquid crystal element is used as a display function layer. However, the present disclosure is not limited to this example, and the display panel 30 may be an organic EL display panel, for example. The IC for detection and the IC for display described above may be provided on a control substrate outside a module. Alternatively, the IC for detection may be provided on the substrate 101 of the fingerprint sensor 10 (refer to FIG. 3 and FIG. 14). The IC for display may be provided on a first substrate 31 of the pixel substrate 30A (refer to FIG. 8).

Figure 3:
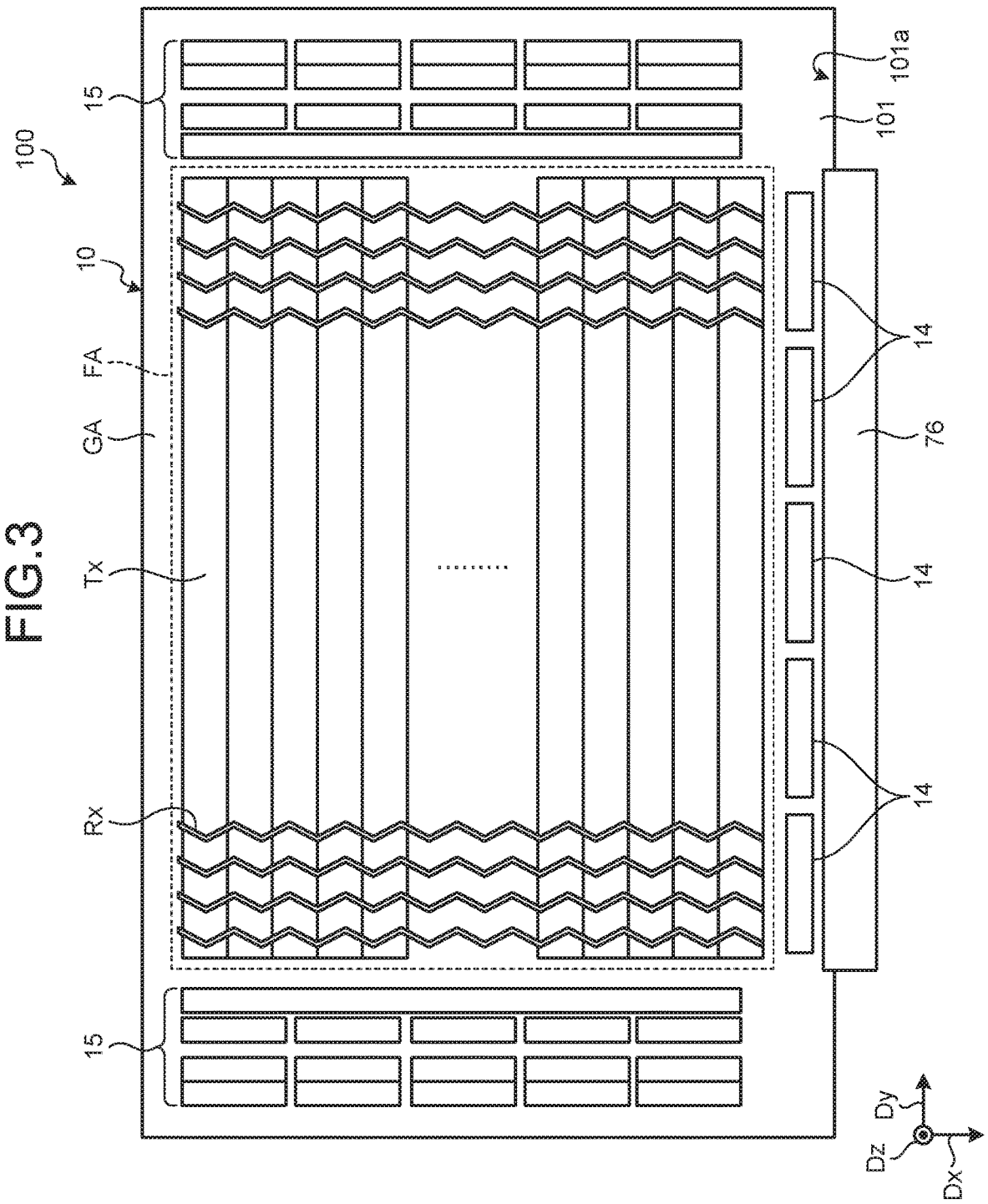
FIG. 3 is a plan view illustrating a configuration example of a fingerprint detection device according to the first embodiment.

FIG. 3 is a plan view illustrating a configuration example of the fingerprint detection device according to the first embodiment. As illustrated in FIG. 3, the fingerprint detection device 100 includes the substrate 101 and the fingerprint sensor 10 provided on the one surface 101a side of the substrate 101. The fingerprint sensor 10 includes drive electrodes Tx and detection electrodes Rx provided on the one surface 101a side of the substrate 101. The substrate 101 is a glass substrate having translucency allowing visible light to pass therethrough. The substrate 101 may be a translucent resin substrate or a resin film formed of a resin such as polyimide. The fingerprint sensor 10 is a sensor having translucency. The drive electrodes Tx are formed of a translucent conductive material such as indium tin oxide (ITO).

The drive electrodes Tx are arranged in a first direction Dx. The drive electrodes Tx extend in a second direction Dy intersecting (e.g., orthogonal to) the first direction Dx. The detection electrodes Rx are arranged in the second direction Dy. The detection electrodes Rx extend in the first direction Dx. In this manner, the detection electrodes Rx extend in a direction intersecting the extension direction of the drive electrodes Tx. The detection electrodes Rx are each connected to the flexible substrate 75 provided on a short side of the frame region GA of the substrate 101 via frame wiring (not illustrated). In the present embodiment, the drive electrodes Tx employ a conductive material having translucency such as ITO. As illustrated in FIG. 3, the drive electrodes Tx and the detection electrodes Rx are provided in the fingerprint detection region FA.

Capacitance is formed at each of intersections between the detection electrodes Rx and the drive electrodes Tx. When a mutual capacitance touch detection operation is performed in the fingerprint sensor 10, a drive electrode driver 15 sequentially selects the drive electrodes Tx in a time division manner, and supplies a drive signal Vs to the selected drive electrode Tx. A detection signal Vdet corresponding to a capacitance change by the recess or protrusion on the surface of the finger or the like being in contact with or in proximity to the cover member 80 is output from the detection electrodes Rx, whereby fingerprint detection is performed. The drive electrode driver 15 may sequentially select each drive electrode block including a plurality of drive electrodes Tx and drive the drive electrodes Tx.

While FIG. 3 illustrates a case in which the various kinds of circuits such as a detection electrode selection circuit 14 and the drive electrode driver 15 are provided in the frame region GA of the substrate 101, this is a mere example. At least part of the various kinds of circuits may be included in the IC for detection mounted on the flexible substrate 76.

Figure 4:
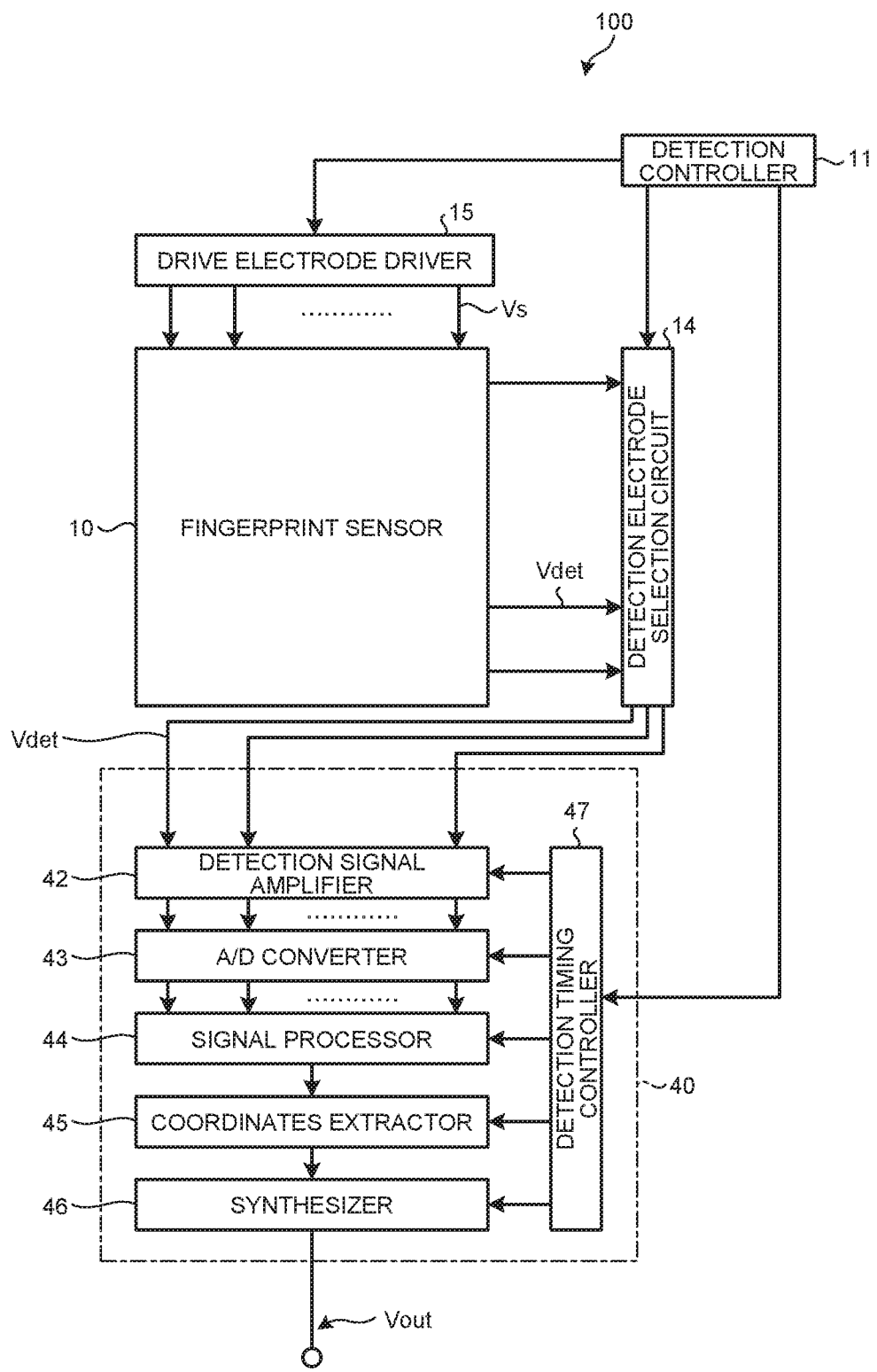
FIG. 4 is a block diagram illustrating a configuration example of the fingerprint detection device.

The following describes a detailed configuration of the fingerprint detection device. FIG. 4 is a block diagram illustrating a configuration example of the fingerprint detection device including the fingerprint sensor. As illustrated in FIG. 4, the fingerprint detection device 100 includes the fingerprint sensor 10, a detection controller 11, the drive electrode driver 15, the detection electrode selection circuit 14, and a detector 40.

The detection controller 11 is a circuit for controlling detection operations of the fingerprint sensor 10. The drive electrode driver 15 is a circuit for supplying a drive signal Vs for detection to the drive electrodes Tx of the fingerprint sensor 10 based on a control signal supplied from the detection controller 11. The detection electrode selection circuit 14 selects the detection electrodes Rx of the fingerprint sensor 10 based on a control signal supplied from the detection controller 11 to connect the selected detection electrodes Rx to the detector 40.

The detector 40 is a circuit for detecting the recess or protrusion on the surface of the finger or the like being in contact with or in proximity to the first surface 80a of the cover member 80 based on a control signal supplied from the detection controller 11 and the detection signal Vdet output from an insulating film 150 to detect the shape of a fingerprint. The detector 40 includes a detection signal amplifier 42, an analog-to-digital (A/D) converter 43, a signal processor 44, a coordinates extractor 45, a synthesizer 46, and a detection timing controller 47. The detection timing controller 47 performs control to cause the detection signal amplifier 42, the A/D converter 43, the signal processor 44, the coordinates extractor 45, and the synthesizer 46 to operate in synchronization with each other based on a control signal supplied from the detection controller 11.

The detection signal Vdet is supplied to the detection signal amplifier 42 of the detector 40 from the fingerprint sensor 10. The detection signal amplifier 42 amplifies the detection signal Vdet. The A/D converter 43 converts an analog signal output from the detection signal amplifier 42 into a digital signal.

The signal processor 44 is a logic circuit for detecting whether the finger is in contact with or in proximity to the fingerprint sensor 10 based on an output signal of the A/D converter 43. The signal processor 44 performs processing to extract a differential signal of detection signals (an absolute value $|\Delta V|$) generated by the finger. The signal processor 44 compares the absolute value $|\Delta V|$ with a certain threshold voltage. If this absolute value $|\Delta V|$ is less than the threshold voltage, the signal processor determines that the finger is in a non-contact state. On the other hand, if the absolute value $|\Delta V|$ is the threshold voltage or greater, the signal processor 44 determines that the finger is in a contact-or-proximity state. In this manner, the detector 40 can detect the contact or proximity of the finger.

The coordinates extractor 45 is a logic circuit that, when the contact or proximity of the finger is detected by the signal processor 44, determines its detected coordinates. The coordinates extractor 45 outputs the detected coordinates to the synthesizer 46. The synthesizer 46 combines the detection signal Vdet output from the fingerprint sensor 10 to generate two-dimensional information indicating the shape of the finger being in contact with or in proximity to the fingerprint sensor 10. The synthesizer 46 outputs the two-dimensional information as output Vout of the detector 40. Alternatively, the synthesizer 46 may generate an image based on the two-dimensional information and make image information serve as the output Vout.

The IC for detection described above functions as the detector 40 illustrated in FIG. 4. Part of the functions of the detector 40 may be included in the IC for display described above or be provided as functions of an external microprocessing unit (MPU).

Figure 5:
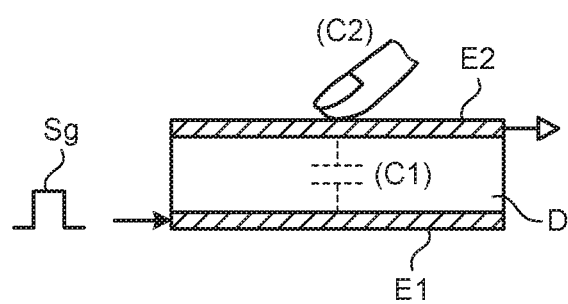
FIG. 5 is a diagram for explaining the basic principle of mutual capacitance detection.
Figure 6:
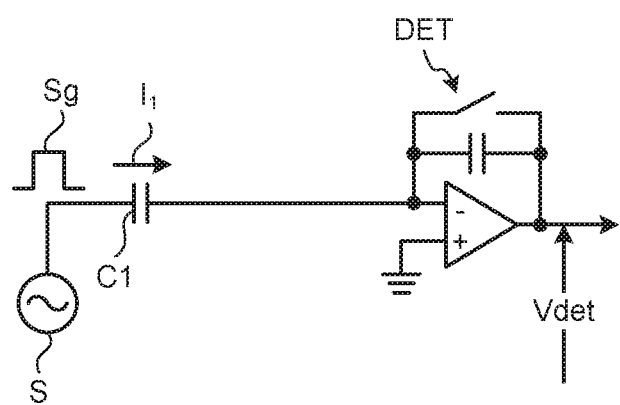
FIG. 6 is a diagram illustrating an exemplary equivalent circuit for explaining the basic principle of the mutual capacitance detection.
Figure 7:
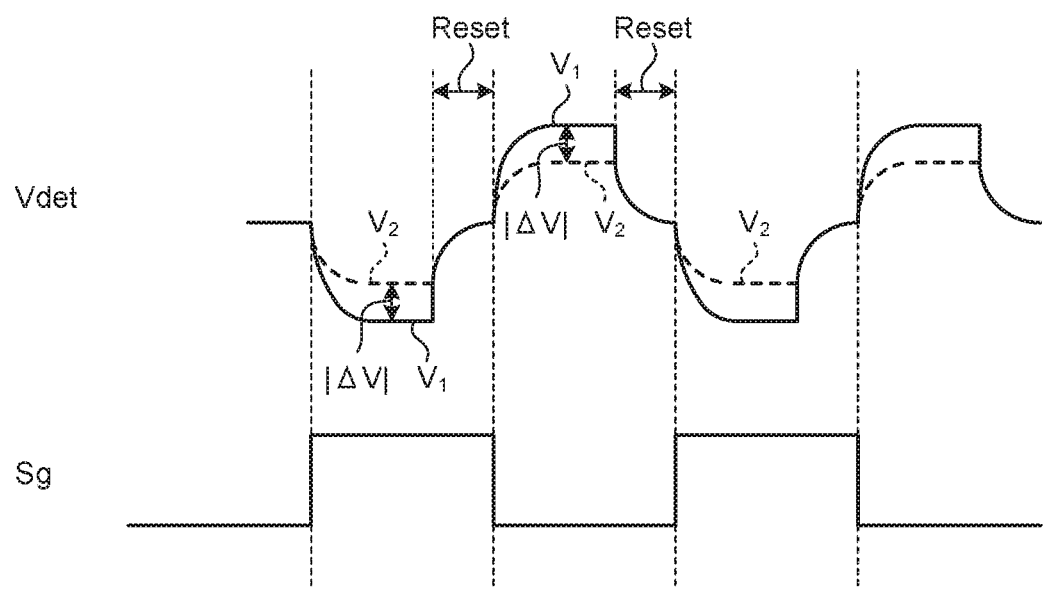
FIG. 7 is a diagram illustrating exemplary waveforms of a drive signal and a detection signal of the mutual capacitance detection.

The fingerprint sensor 10 operates based on the basic principle of capacitance type detection. The following describes the basic principle of mutual capacitance detection by the fingerprint sensor 10 with reference to FIG. 5 to FIG. 7. FIG. 5 is a diagram for explaining the basic principle of mutual capacitance detection. FIG. 6 is a diagram illustrating an exemplary equivalent circuit for explaining the basic principle of the mutual capacitance detection. FIG. 7 is a diagram illustrating exemplary waveforms of a drive signal and a detection signal of the mutual capacitance detection. While the following describes a case in which a finger is in contact with or in proximity to a detection electrode, the present disclosure is not limited to the finger, and a target may be an object including a conductor such as a stylus, for example.

As illustrated in FIG. 5, for example, a capacitance element C1 includes a pair of electrodes facing each other across a dielectric D, i.e., a drive electrode E1, and a detection electrode E2. The capacitance element C1 produces lines of electric force for a fringe extending from ends of the drive electrode E1 toward an upper surface of the detection electrode E2 in addition to lines of electric force (not illustrated) generated between opposing surfaces of the drive electrode E1 and the detection electrode E2. As illustrated in FIG. 6, one end of the capacitance element C1 is connected to an AC signal source (a drive signal source) S, whereas the other end thereof is connected to a voltage detector DET. The voltage detector DET is an integral circuit included in the detector 40 illustrated in FIG. 4, for example.

When the AC signal source S applies an AC rectangular wave Sg at a predetermined frequency (e.g., a frequency of several kilohertz to several hundred kilohertz) to the drive electrode E1 (one end of the capacitance element C1), an output waveform (the detection signal Vdet) as illustrated in FIG. 7 appears via the voltage detector DET connected to the detection electrode E2 (the other end of the capacitance element C1). The AC rectangular wave Sg corresponds to the drive signal Vs input from the drive electrode driver 15 illustrated in FIG. 4.

In a state in which the finger is not in contact with or in proximity to the detection electrode E2 (non-contact state), a current corresponding to the capacitance value of the capacitance element C1 flows with charge and discharge of the capacitance element C1. The voltage detector DET illustrated in FIG. 6 converts fluctuations in a current $I_1$ corresponding to the AC rectangular wave Sg into fluctuations in voltage (a solid line waveform $V_1$ (refer to FIG. 7)).

On the other hand, in a state in which the finger is in contact with or in proximity to the detection electrode E2 (contact state), as illustrated in FIG. 5, capacitance C2 generated by the finger is in contact with or near the detection electrode E2. With this configuration, the lines of electric force for a fringe between the drive electrode E1 and the detection electrode E2 are blocked by the conductor (the finger). Consequently, the capacitance element C1 acts as a capacitance element with a capacitance value smaller than a capacitance value in the non-contact state. As illustrated in FIG. 6 and FIG. 7, the voltage detector DET converts the fluctuations in the current $I_1$ corresponding to the AC rectangular wave Sg into fluctuations in voltage (a dotted line waveform $V_2$).

In this case, the waveform $V_2$ is smaller in amplitude than the waveform $V_1$ described above. With this relation, the absolute value $|\Delta V|$ of a voltage difference between the waveform $V_1$ and the waveform $V_2$ changes in accordance with the influence of an external object being in contact with or in proximity to the detection electrode E2 from the outside such as a finger. In order for the voltage detector DET to accurately detect the absolute value $|\Delta V|$ of the voltage difference between the waveform $V_1$ and the waveform $V_2$, the voltage detector DET preferably operates with a period Reset to reset charge and discharge of a capacitor in accordance with the frequency of the AC rectangular wave Sg by switching in the circuit.

The detector 40 compares the absolute value $|\Delta V|$ with a certain threshold voltage. If the absolute value $|\Delta V|$ is less than the threshold voltage, the detector 40 determines that the finger is in the non-contact state. On the other hand, if the absolute value $|\Delta V|$ is the threshold voltage or greater, the detector 40 determines that the finger is in the contact-or-proximity state. When it is determined that the finger is in the contact-or-proximity state, the detector 40 detects a capacitance change by the recess or protrusion on the surface of the finger based on a difference in the absolute value $|\Delta V|$. The drive electrode E1 illustrated in FIG. 5 corresponds to the drive electrode Tx illustrated in FIG. 3, whereas the detection electrode E2 illustrated in FIG. 5 corresponds to the detection electrode Rx illustrated in FIG. 3.

Figure 8:
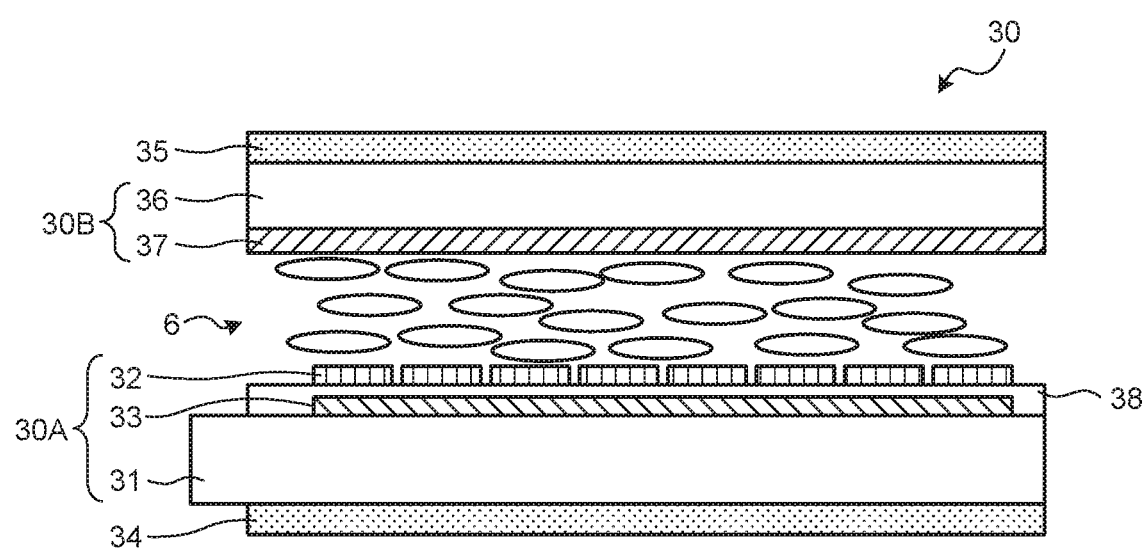
FIG. 8 is a sectional view illustrating a configuration example of a display panel.

FIG. 8 is a sectional view illustrating a configuration example of a display panel. The pixel substrate 30A includes a first substrate 31, pixel electrodes 32, and a common electrode 33. The common electrode 33 is provided on the first substrate 31. The pixel electrodes 32 are provided above the common electrode 33 via an insulating layer 38, and are arranged in a matrix (row-column configuration) in a plan view. The pixel electrodes 32 are provided corresponding to respective subpixels forming each pixel Pix of the display panel 30, and are supplied with pixel signals for performing a display operation. The common electrode 33, to which DC drive signals for display are supplied, functions as a common electrode for the pixel electrodes 32.

In the present embodiment, the common electrode 33, the insulating layer 38, and the pixel electrodes 32 are stacked in this order on the first substrate 31. The polarizing plate 34 is provided below the first substrate 31 via an adhesive layer. Thin film transistors (TFT, not illustrated) serving as switching elements for display are provided to the first substrate 31. For example, a conductive material having translucency such as ITO is used for the pixel electrodes 32 and the common electrode 33.

The arrangement of the pixel electrodes 32 is not limited to the matrix arrangement in which the pixel electrodes 32 are arranged in a first direction and a second direction orthogonal to the first direction, and may employ an arrangement in which adjacent pixel electrodes 32 are shifted from each other in the first direction or the second direction. Alternatively, the present disclosure can employ a configuration in which, with respect to one pixel electrode 32 constituting a pixel column in the first direction, two or three pixel electrodes 32 are arranged on one side of the one pixel electrode 32, according to a difference in shape between adjacent pixel electrodes 32.

The counter substrate 30B includes a second substrate 36 and a color filter 37 formed on one surface of the second substrate 36. The color filter 37 faces a liquid crystal layer 6 in a direction perpendicular to the first substrate 31. Further, the polarizing plate 35 is provided above the second substrate 36 via an adhesive layer. The color filter 37 may be arranged on the first substrate 31. In the present embodiment, each of the first substrate 31 and the second substrate 36 is a glass substrate or a resin substrate, for example.

The liquid crystal layer 6 is provided between the first substrate 31 and the second substrate 36. The liquid crystal layer 6 modulates light passing therethrough in accordance with the state of an electric field, and employs liquid crystals in a transverse electric field mode such as an in-plane switching (IPS) mode including a fringe field switching (FFS) mode. An orientation film may be provided between the liquid crystal layer 6 and the pixel substrate 30A and between the liquid crystal layer 6 and the counter substrate 30B illustrated in FIG. 8.

An illuminator (a backlight, not illustrated) is provided below the first substrate 31. The illuminator has a light source such as a light-emitting diode (LED), for example, and emits light from the light source toward the first substrate 31. The light from the illuminator passes through the pixel substrate 30A, and switching is performed between part of the light to be blocked and not to be emitted and part of the light to be emitted depending on the state of liquid crystals, so that an image is displayed on the display surface (the first surface 80a).

As illustrated in FIG. 2, the display panel 30 is stuck to the fingerprint sensor 10 via the adhesive layer 72 provided on the polarizing plate 35 in the display region AA. The fingerprint sensor 10 is arranged at a position closer to the cover member 80 than the display panel 30 is to the cover member 80 in a direction orthogonal to the second surface 80b of the cover member 80. The provision of the fingerprint sensor 10 closer to the cover member 80 can reduce a distance between the detection electrodes Rx and the first surface 80a serving as the detection surface, in comparison with a case in which detection electrodes for fingerprint detection are provided integrally with the display panel 30, for example. Consequently, the display device 1 of the present embodiment can improve detection performance.

Figure 9:
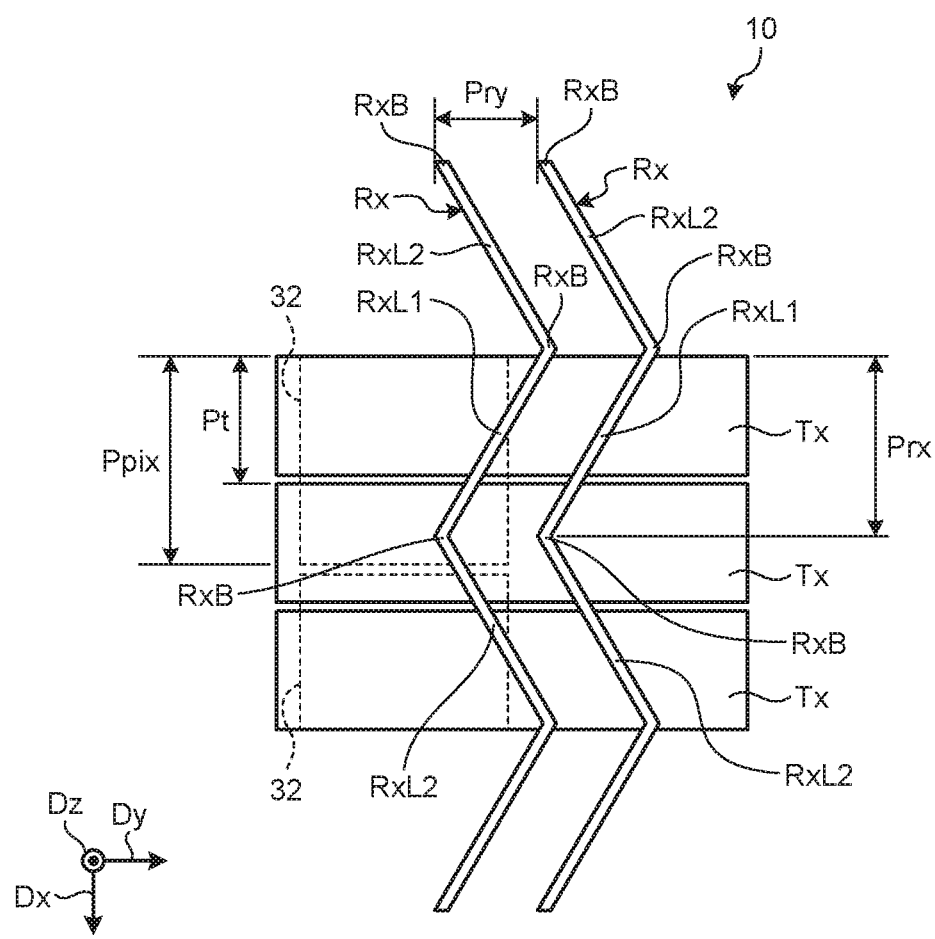
FIG. 9 is a plan view illustrating a configuration example of a fingerprint sensor according to the first embodiment.

FIG. 9 is a plan view illustrating a configuration example of detection electrodes of the fingerprint sensor according to the first embodiment. As illustrated in FIG. 9, the detection electrodes Rx intersect the drive electrodes Tx. When viewed from the normal direction Dz of the substrate 101, the shape of the detection electrode Rx is a zigzag line. The detection electrodes Rx zigzag in the first direction Dx. The detection electrodes Rx each have a plurality of first line portions RxL1, a plurality of second line portions RxL2, and a plurality of bent portions RxB, for example. The second line portions RxL2 extend in a direction intersecting the first line portions RxL1. The bent portions RxB connect the first line portions RxL1 and the second line portions RxL2 to each other.

For example, the first line portions RxL1 extend in a direction intersecting the first direction Dx and the second direction Dy. The second line portions RxL2 also extend in a direction intersecting the first direction Dx and the second direction Dy. The first line portions RxL1 and the second line portions RxL2 are arranged so as to be bilaterally symmetric about a virtual line (not illustrated) parallel to the first direction Dx.

In each of the detection electrodes Rx, an arrangement pitch of bent portions RxB in th first direction Dx is defined as Prx. In adjacent detection electrodes Rx, an arrangement pitch of the bent portions RxB in the second direction Dy is defined as Pry. In the present embodiment, a magnitude relation of Pry<Prx holds, for example.

An arrangement pitch of the drive electrodes Tx in the first direction Dx is defined as Pt. An arrangement pitch in the first direction Dx of the pixel electrodes 32 of the display panel 30 stuck to the fingerprint detection device 100 is defined as Ppix. In the present embodiment, a magnitude relation of the arrangement pitch Pt of the drive electrodes Tx and the arrangement pitch Ppix of the pixel electrodes 32 preferably satisfies the following Expression (1), where n is an integer of 1 or more. With this relation, the fingerprint sensor 10 can reduce the occurrence of unintended patterns (e.g., moire and a light reflecting pattern) in the fingerprint detection region FA.

$$0.6 \times (n-1) \times Ppix \leq Pt \leq 0.4 \times n \times Ppix \tag{1}$$

Figure 10:
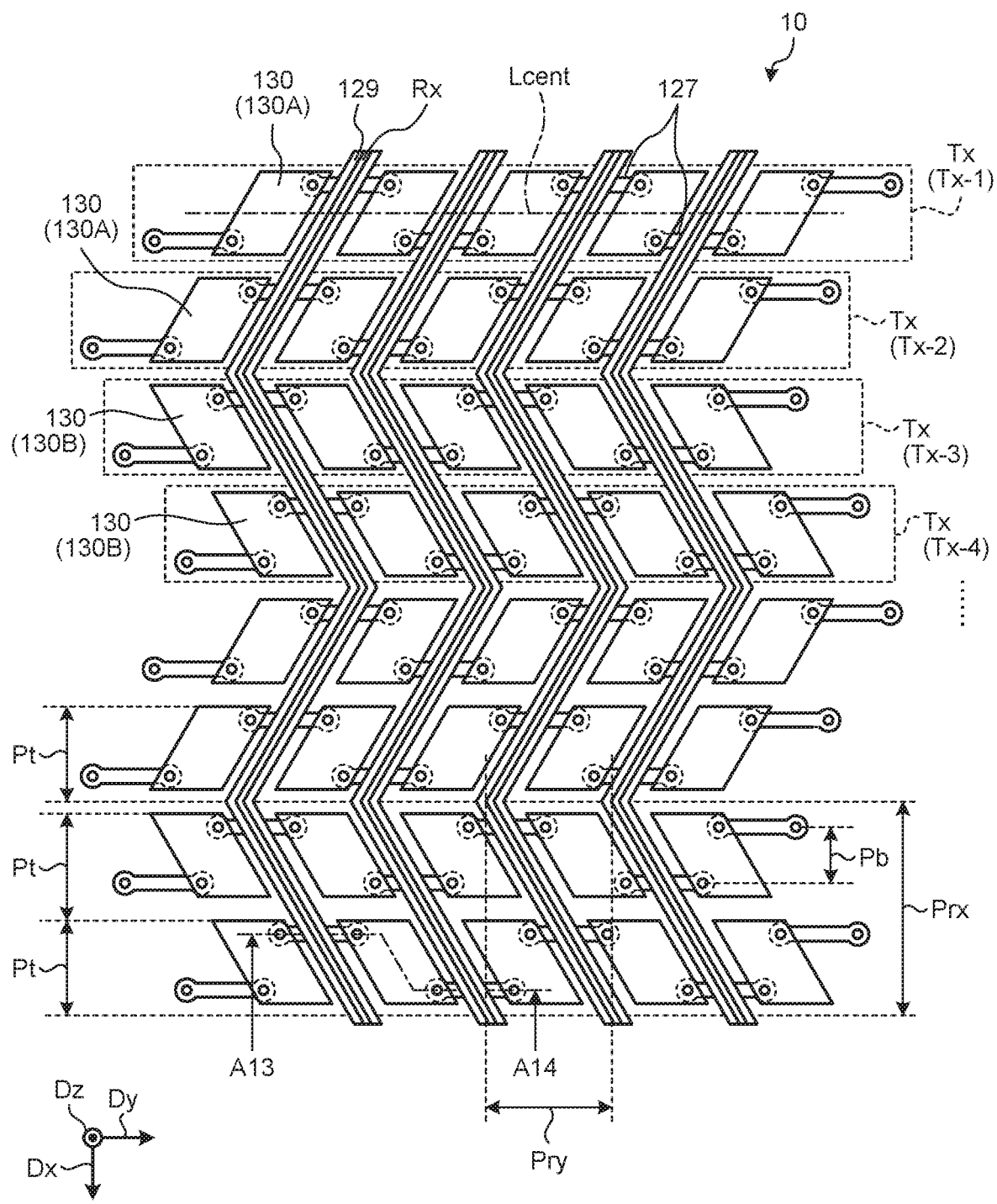
FIG. 10 is a plan view illustrating a configuration example of drive electrodes according to the first embodiment.

The following describes the shape of the drive electrodes Tx more specifically. FIG. 10 is a plan view illustrating a configuration example of the drive electrodes according to the first embodiment. As illustrated in FIG. 10, the drive electrodes Tx (e.g., TX-1, TX-2, TX-3, TX-4, ... ) arranged in the first direction Dx each have a plurality of electrode portions 130 and a plurality of connecting portions 127. In each of the drive electrodes Tx, the electrode portions 130 are arranged in the second direction Dy and are arranged spaced apart from each other. In each of the drive electrodes Tx, the connecting portion 127 connects adjacent electrode portions among the electrode portions 130 to each other. As illustrated in FIG. 10, when viewed from the normal direction Dz of the substrate 101 (refer to FIG. 3), one detection electrode Rx passes through a gap between adjacent electrode portions 130 and intersect the connecting portions 127.

An arrangement pitch of the connecting portions 127 in the first direction Dx is defined as Pb. The arrangement pitch Pb of the connecting portions 127 is preferably 0.5 times the arrangement pitch Pt of the drive electrode Tx. In each of the drive electrodes Tx, the connecting portions 127 are preferably arranged alternately on one side and the other side relative to a central line Lcent parallel to the second direction Dy and passing through the center of the electrode portions 130. With this structure, the connecting portions 127, light transmittance of which is lower than that of the electrode portions 130, are not arranged on a straight line, so that the fingerprint sensor 10 can reduce the occurrence of unintended patterns such as moire.

The longitudinal directions of the connecting portions 127 are preferably aligned in one direction. All of the longitudinal directions of the connecting portions 127 of the drive electrodes Tx are the second direction, for example. This structure uniforms the shape of the connecting portions 127 intersecting the detection electrodes Rx, which makes it easy to uniform capacitance between the drive electrodes Tx and the connecting portions 127.

In the fingerprint sensor 10 illustrated in FIG. 10, the shape of the drive electrodes Tx, the shape of the detection electrodes Rx, and the positional relation thereof are uniform among the electrodes, and thus variations in capacitance of the drive electrodes Tx and variations in capacitance of the detection electrodes Rx are small. Further, there is an advantage that the calculation of coordinates in the fingerprint sensor 10 is easily corrected, for example.

Figure 11:
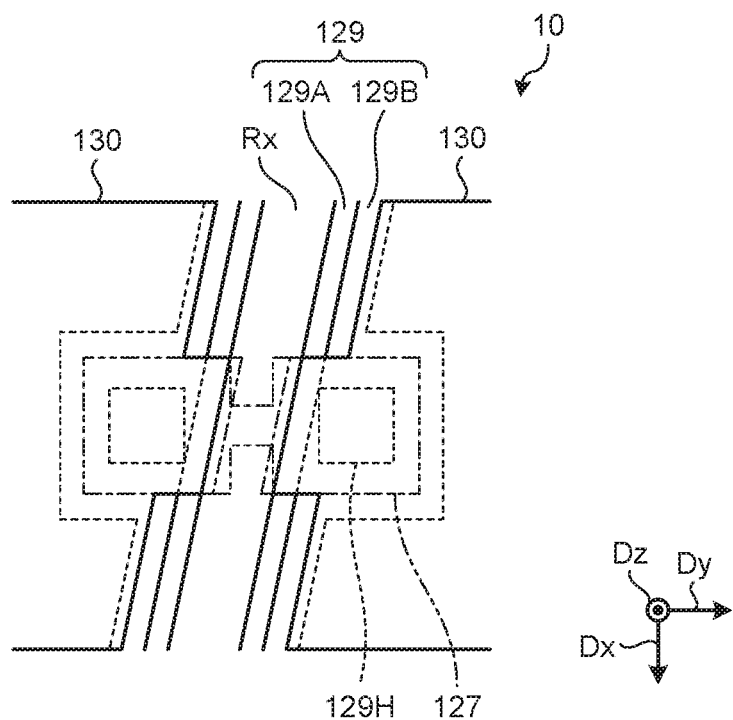
FIG. 11 is a plan view illustrating a drive electrode and a detection electrode according to the first embodiment.
Figure 12:
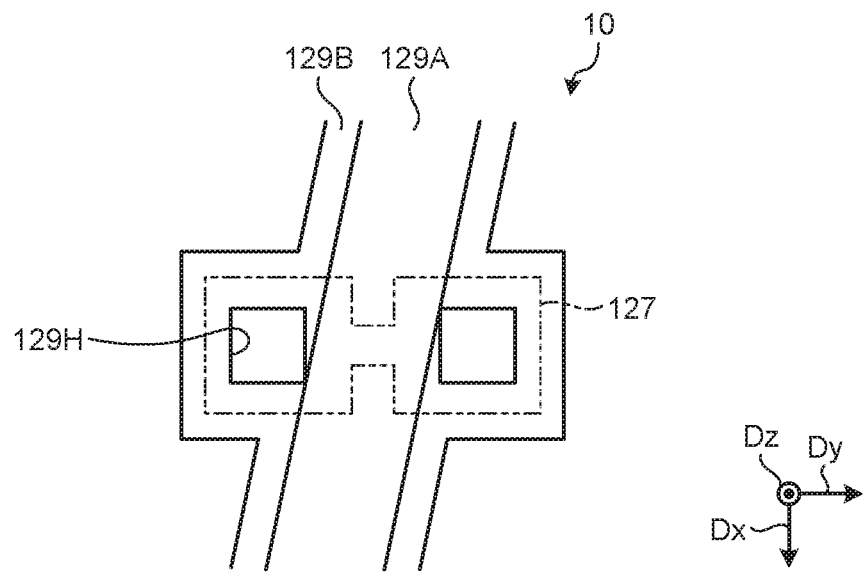
FIG. 12 is a diagram omitting the illustration of electrode portions and the detection electrode in FIG. 11.

FIG. 11 is a plan view illustrating a drive electrode and a detection electrode according to the first embodiment. FIG. 12 is a diagram omitting the illustration of the electrode portions and the detection electrode in FIG. 11. As illustrated in FIG. 11, an insulating layer 129 is arranged between the connecting portion 127 and the detection electrode Rx. The insulating layer 129 is a resin insulating film, for example. The insulating layer 129 includes a first insulating film 129A and a second insulating film 129B thinner than the first insulating film 129A. The second insulating film 129B is provided with a contact hole 129H. As illustrated in FIG. 12, the connecting portion 127 is exposed at the bottom of the contact hole 129H.

Figure 13:
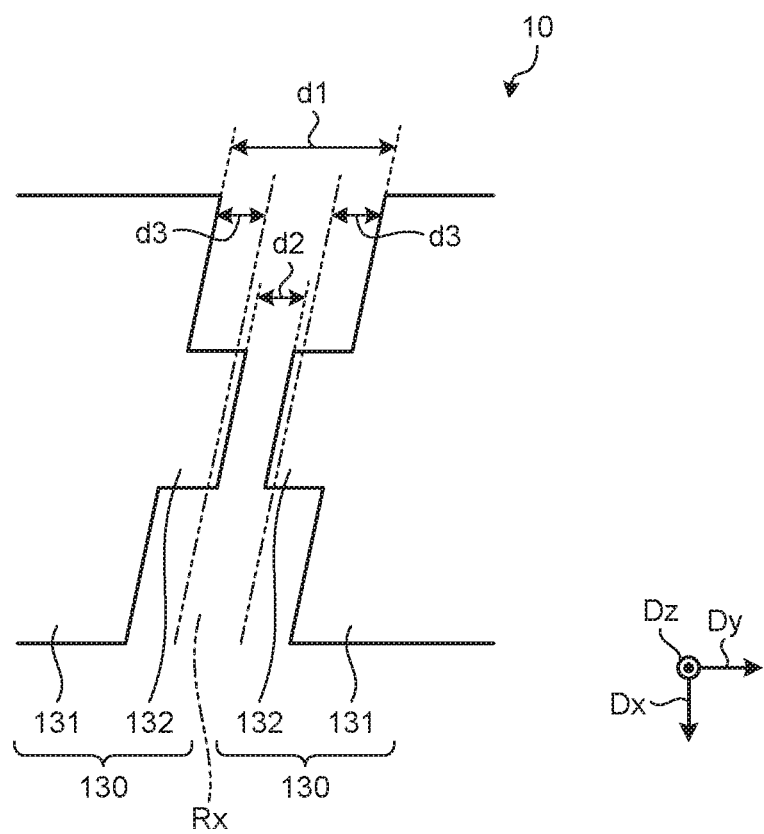
FIG. 13 is a plan view illustrating a configuration example of the electrode portions.

FIG. 13 is a plan view illustrating a configuration example of the electrode portions. As illustrated in FIG. 13, the electrode portion 130 has an electrode main body 131 and a protruding portion 132 in a plan view protruding toward an adjacent electrode portion 130 from the electrode main body 131. The second insulating film 129B is arranged between the protruding portion 132 and the connecting portion 127. The protruding portion 132 is embedded in the contact hole 129H (refer to FIG. 11) provided in the second insulating film 129B. With this structure, the protruding portion 132 is connected to the connecting portion 127 (refer to FIG. 11) via the contact hole 129H. The electrode portions 130 are connected to each other in the second direction Dy via the connecting portions 127.

In the second direction Dy, when a distance between adjacent electrode main bodies 131 is defined as d1, and a distance between adjacent protruding portions 132 is defined as d2, a magnitude relation of d1>d2 holds. When viewed from the normal direction Dz, the detection electrode Rx is arranged so as to overlap with the protruding portions 132 and capacitance generated between the electrode portions 130 and the detection electrode Rx can be reduced, in comparison with a case in which the electrode main bodies 131 and the detection electrode Rx overlap with each other.

As illustrated in FIG. 10, when viewed from the normal direction Dz, the electrode portions 130 have a plurality of shapes. For example, the electrode portions 130 include a first electrode portion 130A and a second electrode portion 130B, the shape of the electrode main body 131 (refer to FIG. 13) of which is different from that of the first electrode portion 130A. When viewed from the normal direction Dz, each of the shape of the electrode main body 131 of the first electrode portion 130A and the shape of the electrode main body 131 of the second electrode portion 130B is a parallelogram. When viewed from the normal direction Dz, the shape of the electrode main body 131 of the first electrode portion 130B is obtained by vertically flipping the shape of the electrode main body 131 of the second electrode portion 130A.

For example, the drive electrodes Tx-1 and Tx-2 intersecting the first line portions RxL1 of the detection electrodes Rx (refer to FIG. 9) include the first electrode portion 130A having two sides parallel to the first line portions RxL1. The drive electrodes Tx-3 and Tx-4 intersecting the second line portions RxL2 of the detection electrodes Rx (refer to FIG. 9) include the second electrode portion 130B having two sides parallel to the second line portions RxL2. With this structure, when viewed from the normal direction Dz, the electrode main bodies 131 can be arranged along the zigzag detection electrode Rx, and a separating distance d3 between the zigzag detection electrode Rx and the electrode main bodies 131 can be a constant length.

Figure 14:
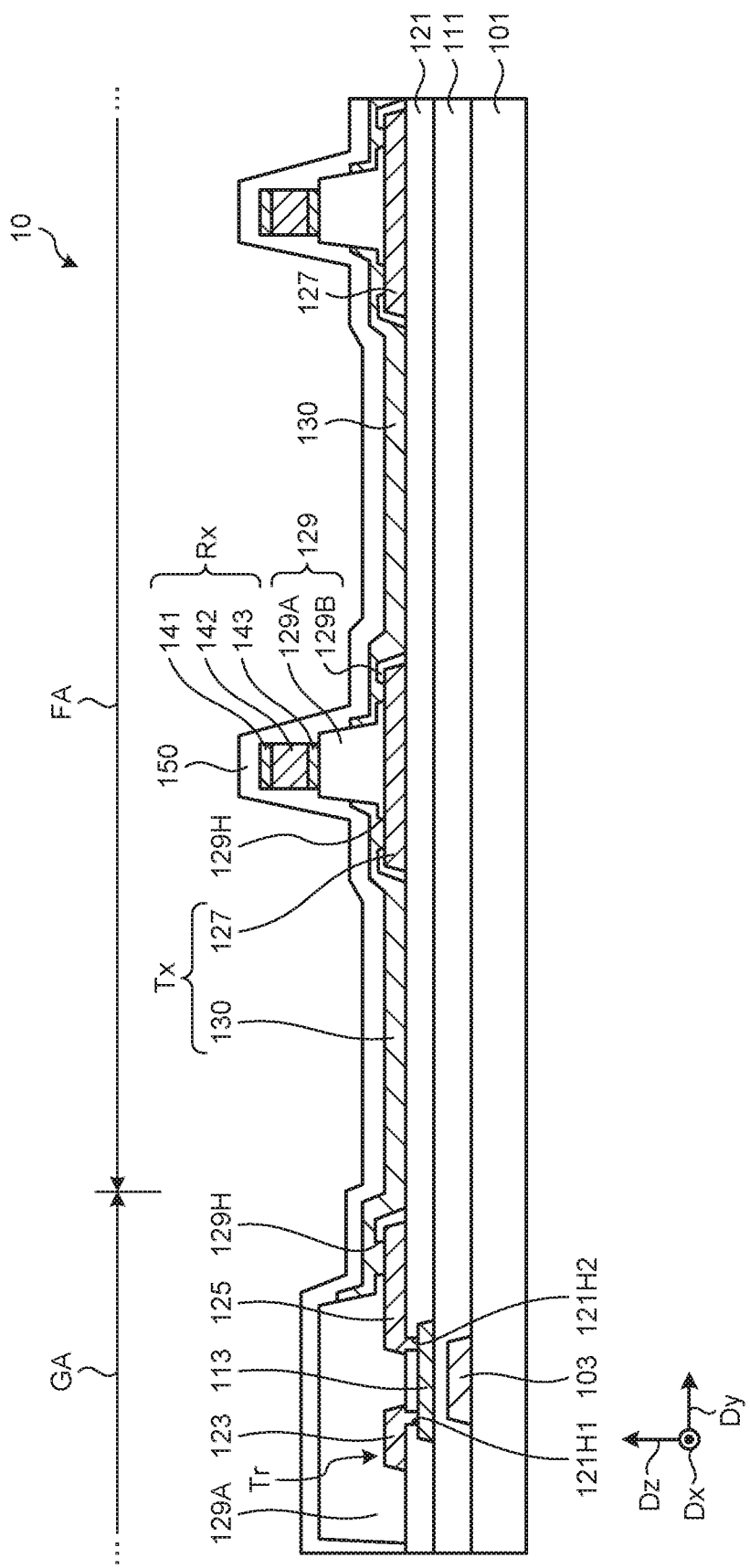
FIG. 14 is a sectional view illustrating a configuration example of the fingerprint sensor.

The following describes a layer structure of the fingerprint sensor. FIG. 14 is a sectional view illustrating a configuration example of the fingerprint sensor. In FIG. 14, the section of the fingerprint detection region FA is obtained by cutting the plan view illustrated in FIG. 10 along the A13-A14 line. In FIG. 14, the section of the frame region GA is obtained by cutting a part including a thin film transistor Tr of the drive electrode driver 15 (refer to FIG. 3). FIG. 14 illustrates the section along the A13-A14 line of the fingerprint detection region FA and the section of the part including the thin film transistor Tr of the frame region GA by schematically connecting these parts in order to show a relation between the layer structure of the fingerprint detection region FA and the layer structure of the frame region GA.

As illustrated in FIG. 14, the fingerprint sensor 10 has the substrate 101, a gate electrode 103 provided on the substrate 101, and a first inter-layer insulating film 111 provided on the substrate 101 to cover the gate electrode 103. The gate electrode 103 is provided in the frame region GA. Aluminum (Al), copper (Cu), silver (Ag), molybdenum (Mo), or an alloy of these materials is used as the material of the gate electrode 103. A silicon oxide film, a silicon nitride film, or a silicon oxide nitride film is used as the material of the first inter-layer insulating film 111. The first inter-layer insulating film 111 is not limited to a single layer and may be a film with a multilayered structure. The first inter-layer insulating film 111 may be a film with a multilayered structure in which a silicon nitride film is formed on a silicon oxide film, for example.

The fingerprint sensor 10 includes: a semiconductor layer 113 formed on the first inter-layer insulating film 111; and a second inter-layer insulating film 121 formed on the first inter-layer insulating film 111 to cover the semiconductor layer 113. The second inter-layer insulating film 121 is provided with contact holes 121H1 and 121H2. The semiconductor layer 113 is exposed at the bottom of the contact holes 121H1 and 121H2. A polysilicon or an oxide semiconductor is used as the material of the semiconductor layer 113. A silicon oxide film, a silicon nitride film, or a silicon oxide nitride film is used as the material of the second inter-layer insulating film 121. The second inter-layer insulating film 121 is not limited to a single layer and may be a film with a multilayered structure. The second inter-layer insulating film 121 may be a film with a multilayered structure in which a silicon nitride film is formed on a silicon oxide film, for example.

The fingerprint sensor 10 includes a source electrode 123, a drain electrode 125, and the connecting portions 127 provided on the second inter-layer insulating film 121. The source electrode 123 is embedded in the contact hole 121H1. The drain electrode 125 is embedded in the contact hole 121H2. With this structure, the source electrode 123 is connected to the semiconductor layer 113 via the contact hole 121H1. The drain electrode 125 is connected to the semiconductor layer 113 via the contact hole 121H2. Titanium aluminum (TiAl), which is an alloy of titanium and aluminum, is used as the materials of the source electrode 123, the drain electrode 125, and the connecting portions 127.

The gate electrode 103, the semiconductor layer 113, the source electrode 123, and the drain electrode 125 described above are provided in the frame region GA. The gate electrode 103, the semiconductor layer 113, the source electrode 123, and the drain electrode 125 constitute the thin film transistor Tr in the frame region GA.

The insulating layer 129 is provided on the second inter-layer insulating film 121. As described above, the insulating layer 129 includes the first insulating film 129A and the second insulating film 129B thinner than the first insulating film 129A. The first insulating film 129A provided in the frame region GA covers the source electrode 123 and the drain electrode 125. The first insulating film 129A provided in the frame region GA is provided with the contact hole 129H. The first insulating film 129A provided in the fingerprint detection region FA covers part of the connecting portion 127 positioned under the detection electrode Rx. The second insulating film 129B provided in the fingerprint detection region FA covers part of the connecting portion 127 positioned under the electrode portion 130. As described above, the second insulating film 129B is provided with the contact hole 129H.

A resin film is used as the insulating layer 129, for example. Since the resin film has a high refractive index, the resin film serving as the insulating layer 129 is preferably not arranged in the display region AA as much as possible. Not arranging the resin film in the display region AA as much as possible improves the visibility of an image displayed on the display region AA. As described above, in the display device 1 of the present embodiment, the display region AA and the fingerprint detection region FA match with each other or substantially match with each other. In the configuration in FIG. 14, only the second insulating film 129B, which is a thin film, is arranged as the insulating layer 129 in the display region AA. Consequently, the visibility of the image displayed on the display region AA improves.

Further, the electrode portions 130 are provided on the second inter-layer insulating film 121. In the fingerprint detection region FA, the peripheral parts of the electrode portions 130 (e.g., the protruding portions 132 illustrated in FIG. 13) are embedded in the contact hole 129H. With this structure, the electrode portions 130 are connected to the connecting portions 127 via the contact hole 129H. In this example, the electrode portions 130 are in contact with the second inter-layer insulating film 121.

In the fingerprint detection region FA, the detection electrodes Rx are provided on the first insulating film 129A. The first insulating film 129A insulates the detection electrodes Rx and the drive electrodes Tx from each other. The detection electrode Rx includes a first metallic layer 141, a second metallic layer 142, and a third metallic layer 143, for example. The second metallic layer 142 is provided on the third metallic layer 143, and the first metallic layer 141 is provided on the second metallic layer 142. Molybdenum or a molybdenum alloy is used as the materials of the first metallic layer 141 and the third metallic layer 143, for example. Aluminum or an aluminum alloy is used as the material of the second metallic layer 142. Molybdenum or a molybdenum alloy forming the first metallic layer 141 has a reflectance of visible light lower than that of aluminum or an aluminum alloy forming the second metallic layer 142.

The insulating film 150 is provided above the insulating layer 129, the electrode portions 130, and the detection electrodes Rx. The insulating film 150 covers upper surfaces and side surfaces of the detection electrodes Rx. A film with a high refractive index and a low reflectance such as a silicon nitride film is used as the insulating film 150. Alternatively, the insulating film 150 may be a light-shielding resin film (e.g., a black resin film).

Figure 15:
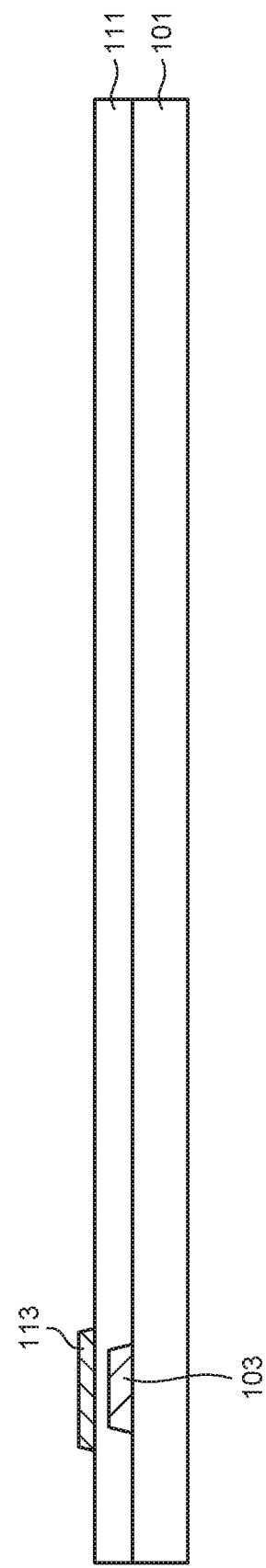
FIG. 15 is a sectional view illustrating a method for manufacturing the fingerprint sensor according to the first embodiment.

The following describes a method for manufacturing the fingerprint sensor illustrated in FIG. 14 in order of process. FIG. 15 to FIG. 22 are sectional views each illustrating a method for manufacturing the fingerprint sensor according to the first embodiment. As illustrated in FIG. 15, first, a manufacturing apparatus (not illustrated) forms a conductive film (not illustrated) such as aluminum on the substrate 101. The conductive film is formed by sputtering, for example.

Subsequently, the manufacturing apparatus forms the gate electrode 103 by patterning the conductive film by photolithography technique and dry etching technique. The manufacturing apparatus forms a resist (not illustrated) on the conductive film, for example. The resist, which is patterned by the photolithography, is formed into a shape covering an area in which the gate electrode 103 is formed, and exposing the other area. Subsequently, the manufacturing apparatus removes the conductive film in the area exposed from the resist by the dry etching technique. With this operation, the gate electrode 103 is formed out of the conductive film. After forming the gate electrode 103, the manufacturing apparatus removes the resist.

Subsequently, the manufacturing apparatus forms the first inter-layer insulating film 111 on the substrate 101. The first inter-layer insulating film 111 is formed by chemical vapor deposition (CVD), for example. With this operation, the gate electrode 103 is covered with the first inter-layer insulating film 111. Subsequently, the manufacturing apparatus forms a semiconductor film (not illustrated) on the first inter-layer insulating film 111. The semiconductor film is formed by the CVD, for example. Subsequently, the manufacturing apparatus patterns the semiconductor film by the photolithography technique and the dry etching technique. With this operation, the manufacturing apparatus forms the semiconductor layer 113 out of the semiconductor film.

Subsequently, the manufacturing apparatus forms the second inter-layer insulating film 121 on the first inter-layer insulating film 111. The second inter-layer insulating film 121 is formed by the CVD, for example. With this operation, the semiconductor layer 113 is covered with the second inter-layer insulating film 121.

Subsequently, the manufacturing apparatus forms the contact holes 121H1 and 121H2 in the second inter-layer insulating film 121. The manufacturing apparatus forms a resist (not illustrated) on the second inter-layer insulating film 121, for example. The resist, which is patterned by the photolithography, is formed into a shape exposing areas in which the contact holes 121H1 and 121H2 are formed, and covering the other area. Subsequently, the manufacturing apparatus removes the second inter-layer insulating film 121 in the area exposed from the resist by the dry etching technique. With this operation, the contact holes 121H1 and 121H2 are formed in the second inter-layer insulating film 121. After forming the contact holes 121H1 and 121H2, the manufacturing apparatus removes the resist.

Figure 17:
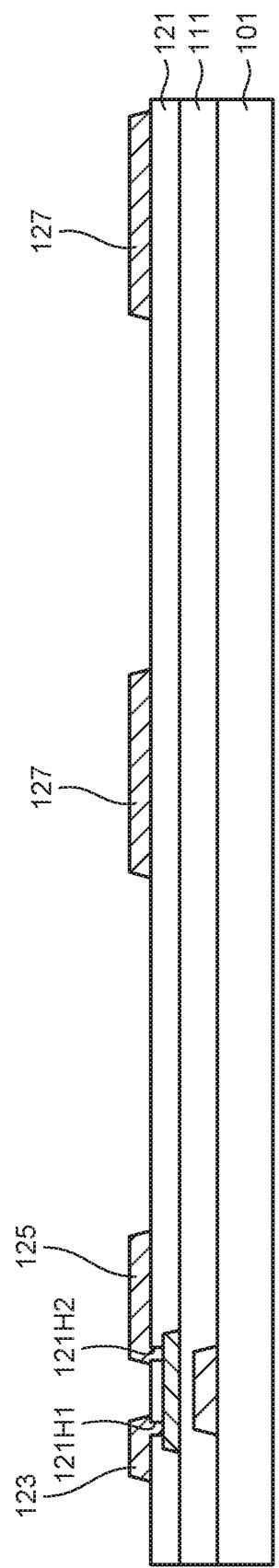
FIG. 17 is a sectional view illustrating the method for manufacturing the fingerprint sensor according to the first embodiment.

Subsequently, the manufacturing apparatus forms a metallic film (not illustrated) such as titanium aluminum on the second inter-layer insulating film 121. The metallic film is formed by the sputtering, for example. Subsequently, the manufacturing apparatus patterns the metallic film by the photolithography technique and the dry etching technique. With this operation, as illustrated in FIG. 17, the manufacturing apparatus forms the source electrode 123, the drain electrode 125, and the connecting portions 127 out of the metallic film.

Figure 18:
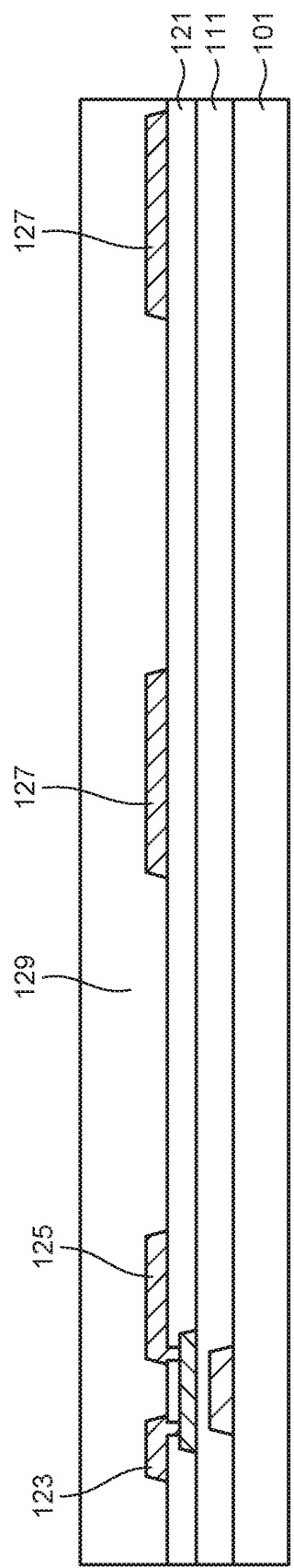
FIG. 18 is a sectional view illustrating the method for manufacturing the fingerprint sensor according to the first embodiment.

Subsequently, as illustrated in FIG. 18, the manufacturing apparatus forms the insulating layer 129 on the second inter-layer insulating film 121. The insulating layer 129 is a resin film, for example, and is a positive resist, for example. The insulating layer 129 is formed by spin coating technique, for example. The insulating layer 129 covers the source electrode 123, the drain electrode 125, and the connecting portions 127.

Figure 19:
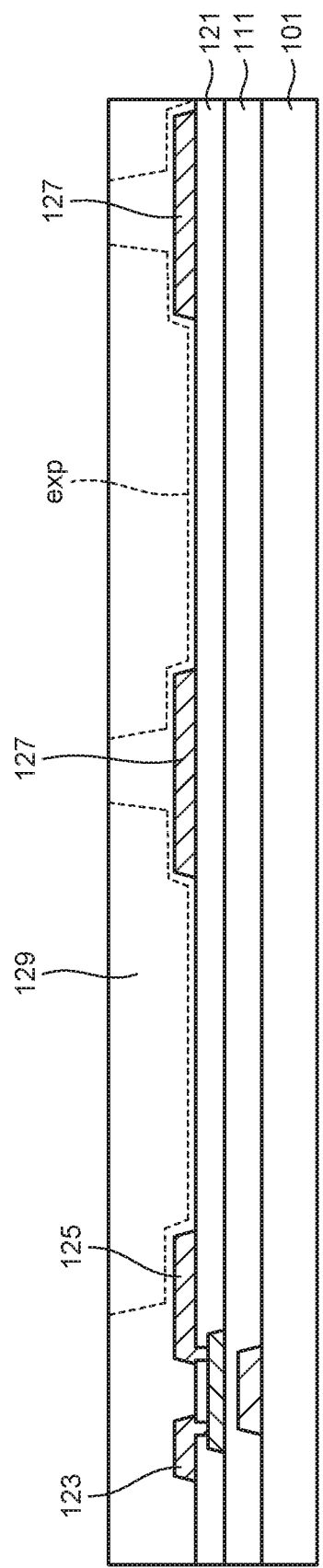
FIG. 19 is a sectional view illustrating the method for manufacturing the fingerprint sensor according to the first embodiment.

Subsequently, the manufacturing apparatus performs first exposure processing on the insulating layer 129. The first exposure processing is half exposure. As illustrated in FIG. 19, in the half exposure, part of the insulating layer 129 ranging from an upper surface of the insulating layer 129 to a halfway position exp in the thickness direction of the insulating layer 129 is exposed. Subsequently, the manufacturing apparatus performs second exposure processing on the insulating layer 129. With this operation, the part of the insulating layer 129 in which the contact hole 129H (refer to FIG. 14) is formed is exposed.

Figure 20:
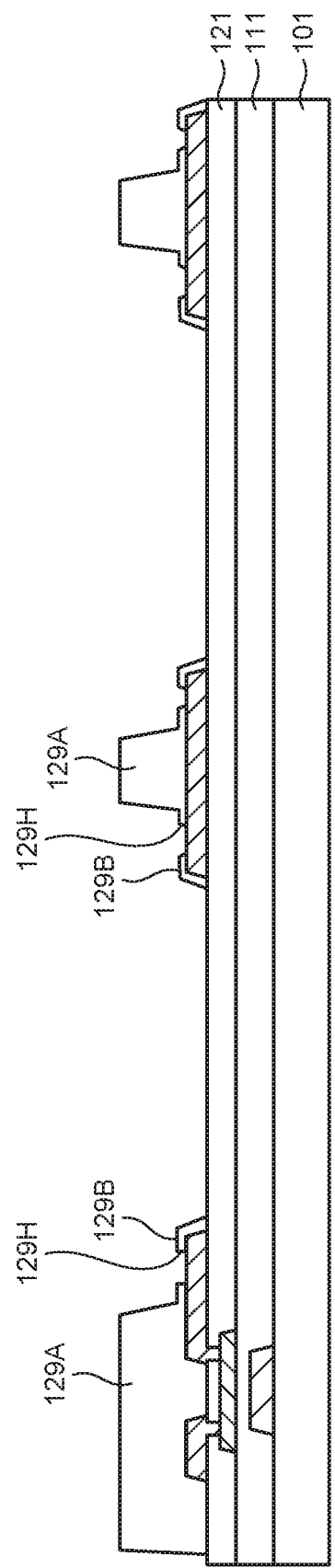
FIG. 20 is a sectional view illustrating the method for manufacturing the fingerprint sensor according to the first embodiment.

Subsequently, the manufacturing apparatus performs developing processing on the insulating layer 129. Through the developing processing, the part exposed through the first exposure processing and the part exposed through the second exposure processing are removed from the insulating layer 129. Consequently, as illustrated in FIG. 20, the first insulating film 129A and the second insulating film 129B thinner than the first insulating film 129A are formed out of the insulating layer 129. The contact hole 129H is formed in the second insulating film 129B.

Figure 21:
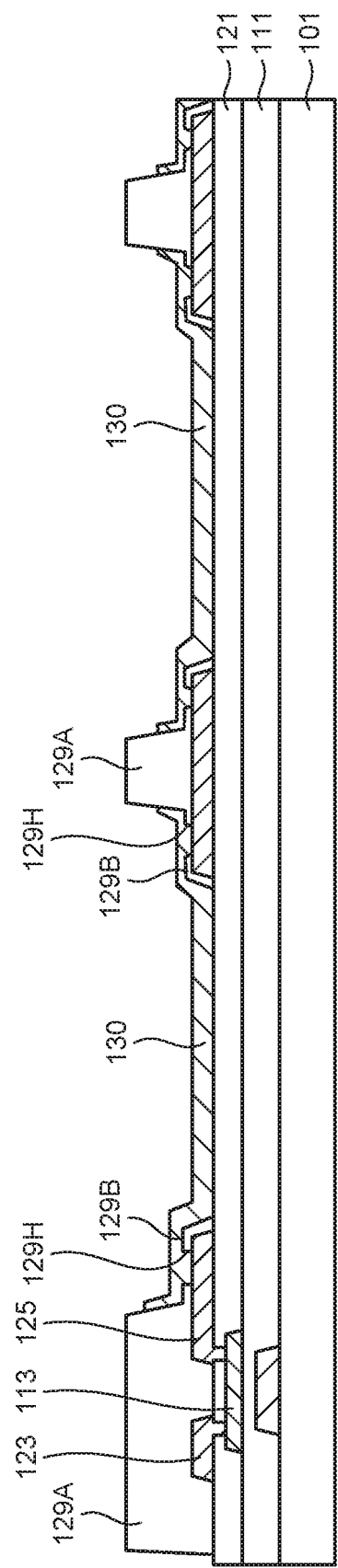
FIG. 21 is a sectional view illustrating the method for manufacturing the fingerprint sensor according to the first embodiment.

Subsequently, the manufacturing apparatus forms a conductive film such as ITO (not illustrated) above the substrate 101. The conductive film is formed by the sputtering, for example. Subsequently, the manufacturing apparatus patterns the conductive film by the photolithography technique and the dry etching technique. With this operation, as illustrated in FIG. 21, the manufacturing apparatus forms the electrode portions 130 out of the conductive film.

Figure 22:
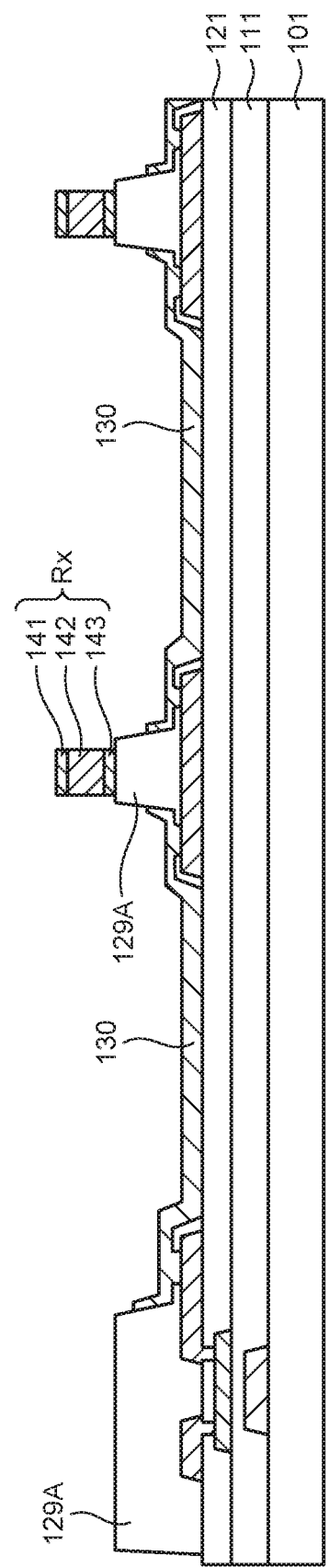
FIG. 22 is a sectional view illustrating the method for manufacturing the fingerprint sensor according to the first embodiment.

Subsequently, the manufacturing apparatus forms a metallic film with a multilayered structure (not illustrated) above the substrate 101. The metallic film with the multilayered structure is a film with molybdenum or a molybdenum alloy, aluminum or an aluminum alloy, and molybdenum or a molybdenum alloy stacked in this order from the substrate 101, for example. The metallic film is formed by the sputtering, for example. Subsequently, the manufacturing apparatus patterns the metallic film by the photolithography technique and the dry etching technique. With this operation, as illustrated in FIG. 22, the manufacturing apparatus forms the detection electrode Rx including the first metallic layer 141, the second metallic layer 142, and the third metallic layer 143.

Subsequently, the manufacturing apparatus forms the insulating film 150 (refer to FIG. 14) above the substrate 101. The insulating film 150 is formed by the CVD or the like. Through the foregoing processes, the fingerprint sensor 10 illustrated in FIG. 14 is completed.

As described above, the fingerprint sensor 10 according to the first embodiment includes the drive electrodes Tx and the detection electrodes Rx both provided on the one surface 101a side of the substrate 101. The drive electrodes Tx are arranged in the first direction Dx. The detection electrodes Rx are arranged in the second direction Dy intersecting the first direction Dx. The fingerprint sensor 10 includes the insulating layer 129 provided in the normal direction Dz of the substrate 101 between the drive electrodes Tx and the respective detection electrodes Rx. In the normal direction of the substrate 101, the detection electrodes Rx intersect the drive electrodes Tx. The detection electrode Rx has the first metallic layer 141 and the second metallic layer 142 positioned closer to the one surface 101a than the first metallic layer 141 is to the one surface 101a. The first metallic layer 141 has a reflectance of visible light lower than that of the second metallic layer 142. This structure can reduce the reflection of light coming from the cover member 80 side (hereinafter, incident light) on the detection electrodes Rx, thereby making the detection electrodes Rx less noticeable. Consequently, the fingerprint sensor 10 can reduce the occurrence of unintended patterns such as moire.

The fingerprint sensor 10 includes the insulating film 150 provided on the one surface 101a side of the substrate 101. The insulating film 150 covers the detection electrodes Rx. The insulating film 150 is a film with a high refractive index and a low reflectance and is a silicon nitride film, for example. Alternatively, the insulating film 150 is a light-shielding resin film (e.g., a black resin film). With this structure, the fingerprint sensor 10 can further reduce the reflection of light.

Figure 23:
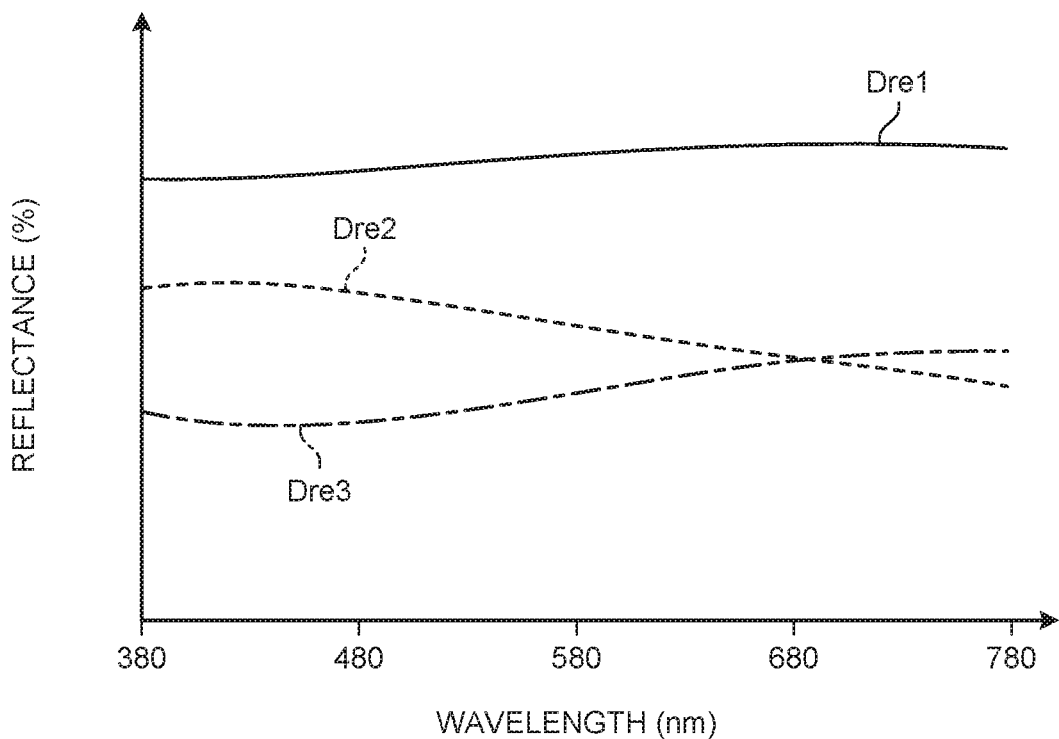
FIG. 23 is a diagram illustrating a relation between the thickness of an insulating film covering the detection electrodes and the reflectance of light.

FIG. 23 is a diagram illustrating a relation between the thickness of an insulating film covering the detection electrodes and the reflectance of light. The horizontal axis of FIG. 23 indicates a wavelength (nm) of light incident on the fingerprint detection region FA, where 380 nm to 780 nm correspond to a wavelength range of visible light. The vertical axis of FIG. 23 indicates the reflectance of light coming from the detection electrodes Rx. In FIG. 23, Dre1 is measured data when no silicon nitride film is provided on the detection electrodes Rx so that the detection electrodes Rx are exposed to the air. Dre2 is measured data when a silicon nitride film with a thickness of 100 nm is provided on the detection electrodes Rx. Dre3 is measured data when a silicon nitride film with a thickness of 50 nm is provided on the detection electrodes Rx. As illustrated in FIG. 23, in the wavelength range of visible light, the data Dre2 and Dre3 have a reflectance lower than that of the data Dre1. Consequently, the fingerprint sensor 10 can further reduce the reflection of light by having the insulating film 150. As illustrated in FIG. 23, there is a correlation between the thickness of the silicon nitride film and the reflectance of visible light. Consequently, a designer of the fingerprint detection device may set the thickness of the insulating film 150 so as to make the reflectance of visible light a desired value.

The electrode portions 130 are translucent electrodes, whereas the detection electrodes Rx are metallic thin lines. This structure can reduce resistance and capacitance of the detection electrodes Rx. The detection electrodes Rx are metallic thin lines and are thus small in electrode width. This structure can reduce the area covered with the detection electrodes Rx. Consequently, the fingerprint sensor 10 can increase the aperture of the fingerprint detection region FA and increase the translucency of the fingerprint detection region FA.

The insulating layer 129 includes: the first insulating film 129A arranged between the connecting portion 127 and the detection electrode Rx in the normal direction Dz of the substrate 101; and the second insulating film 129B arranged between the connecting portion 127 and the electrode portion 130. The second insulating film 129B is thinner than the first insulating film 129A. This structure allows the fingerprint sensor 10 to reduce a level difference of the electrode portion 130 in comparison with a case in which the electrode portion 130 is arranged on the first insulating film 129A. This structure can lower the probability of disconnection in the electrode portion 130. The first insulating film 129A arranged between the connecting portion 127 and the detection electrode Rx is larger in thickness than the second insulating film 129B, and thus can reduce capacitance generated between the detection electrodes Rx and the drive electrodes Tx.

The fingerprint sensor 10 includes: the first inter-layer insulating film 111 provided on the one surface 101a of the substrate 101; and the second inter-layer insulating film 121 provided on the first inter-layer insulating film 111 in the fingerprint detection region FA. The drive electrodes Tx are provided on the second inter-layer insulating film. The sum of the thickness of the first inter-layer insulating film 111, the thickness of the second inter-layer insulating film 121, and the thickness of the drive electrode Tx is preferably 150 nm or less. This structure can reduce the reflection of light incident on the drive electrodes Tx.

Second Embodiment

The above has described the first embodiment in which the connecting portion 127 is connected to the electrode portion 130 via the contact hole 129H. However, in the present embodiment, the connecting portion 127 may be connected to the electrode portion 130 without via a contact hole. The electrode portions 130 adjacent to each other in the second direction Dy may be connected to each other via a conductive film formed simultaneously with the electrode portions 130 at the same process.

Figure 24:
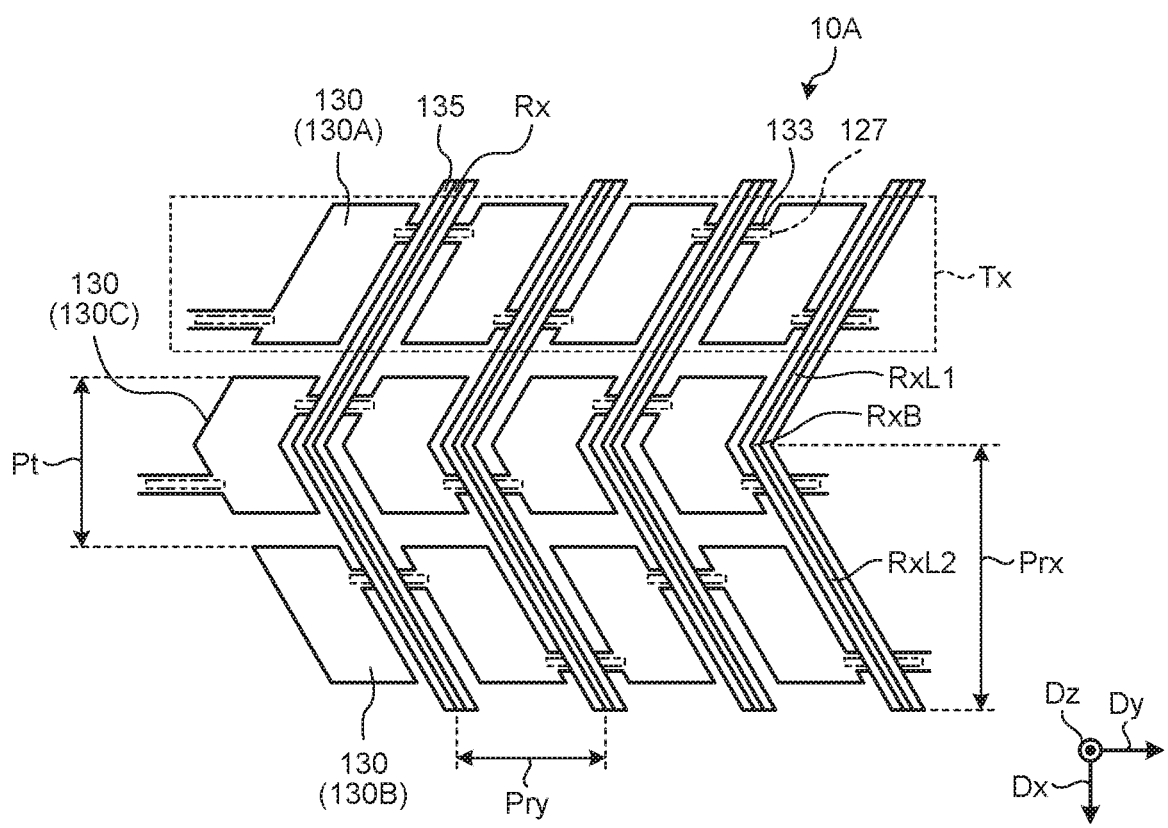
FIG. 24 is a plan view illustrating a configuration example of a fingerprint sensor according to a second embodiment.
Figure 25:
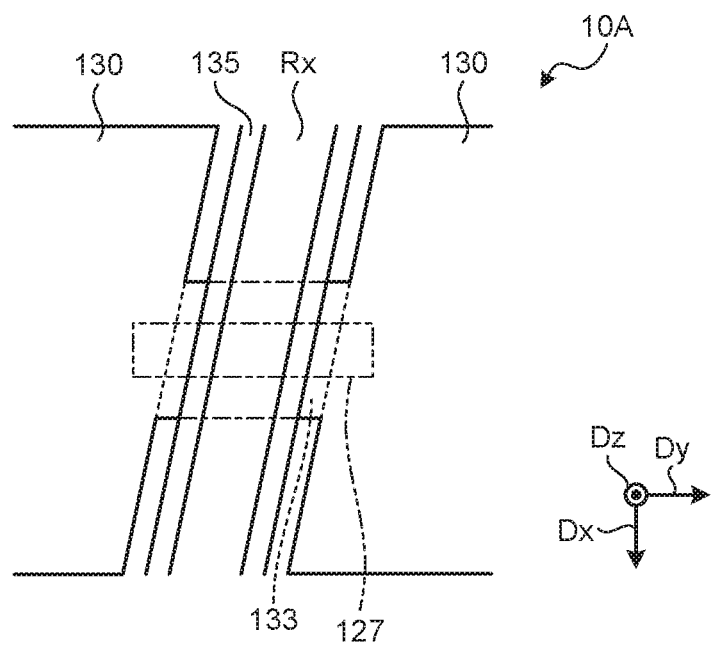
FIG. 25 is a plan view illustrating the drive electrode and the detection electrode according to the second embodiment.
Figure 26:
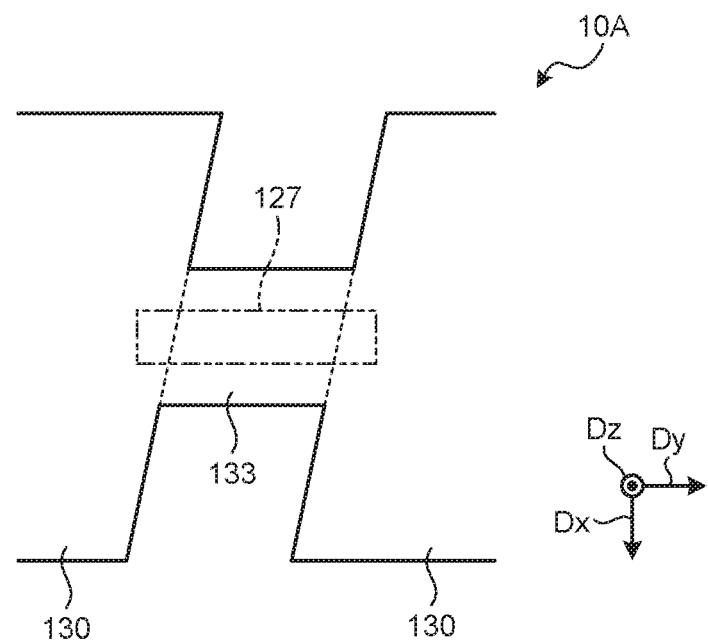
FIG. 26 is a diagram omitting the illustration of the detection electrode and an insulating film in FIG. 25.
Figure 27:
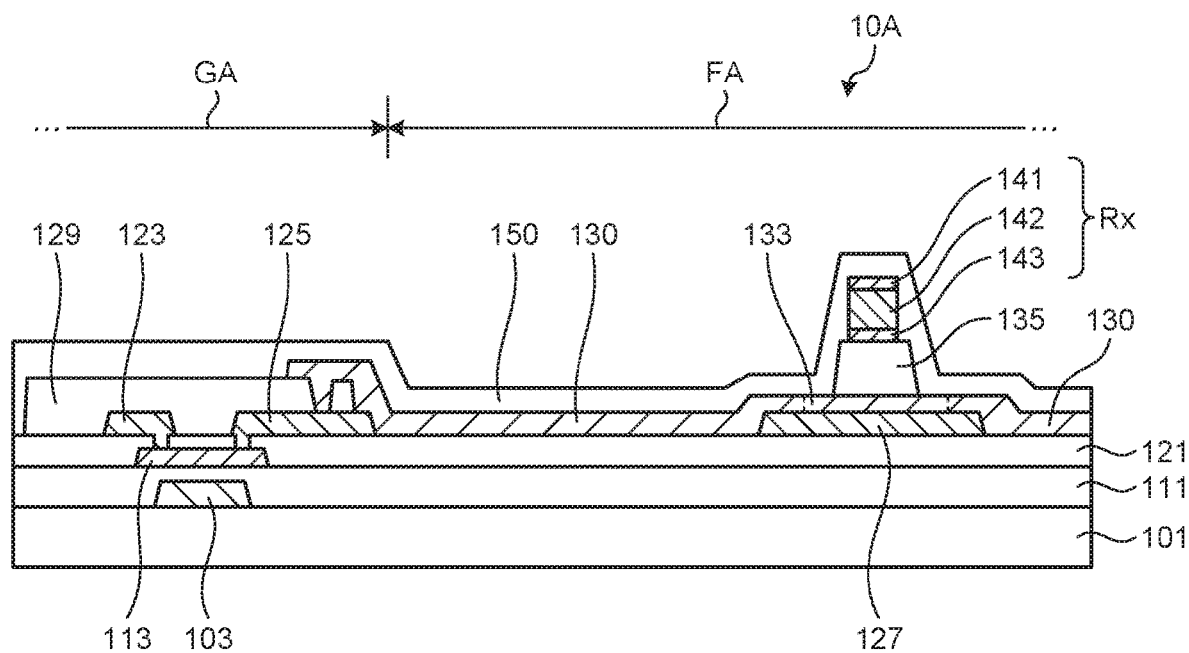
FIG. 27 is a sectional view illustrating a configuration example of the fingerprint sensor according to the second embodiment.
Figure 28:
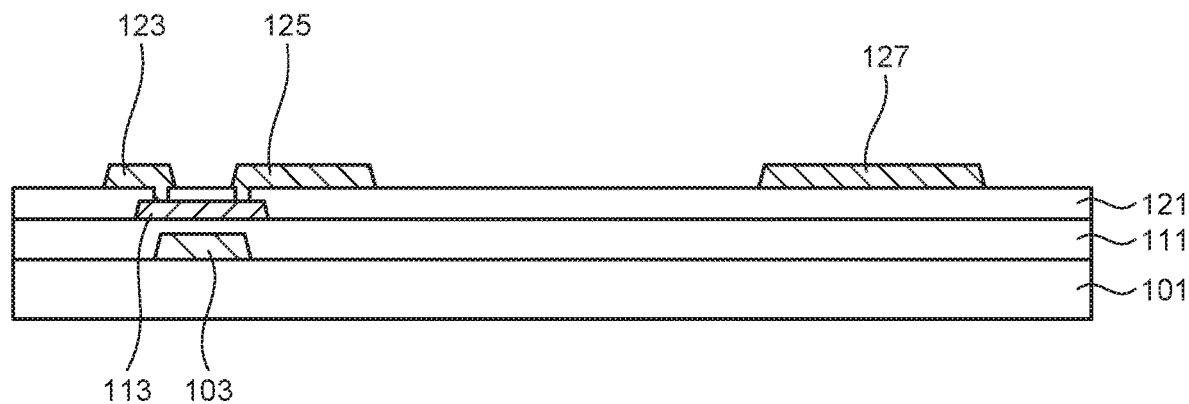
FIG. 28 is a sectional view illustrating a method for manufacturing the fingerprint sensor according to the second embodiment.

FIG. 24 is a plan view illustrating a configuration example of a fingerprint sensor according to a second embodiment. FIG. 25 is a plan view illustrating the drive electrode and the detection electrode according to the second embodiment. FIG. 26 is a diagram omitting the illustration of the detection electrode and the insulating film in FIG. 25. FIG. 27 is a sectional view illustrating a configuration example of the fingerprint sensor according to the second embodiment.

As illustrated in FIG. 24, in this fingerprint sensor 10A according to the second embodiment, one drive electrode Tx has a plurality of electrode portions 130, a plurality of connecting portions (hereinafter, first connecting portions) 127, and a plurality of second connecting portions 133. In one drive electrode Tx, the electrode portions 130 are arranged in the second direction Dy and are spaced apart from each other. In one drive electrode Tx, the first connecting portions 127 and the second connecting portions 133 each connect adjacent electrode portions among the electrode portions 130 to each other. As illustrated in FIG. 27, for example, the second connecting portion 133 is provided above the first connecting portion 127.

As illustrated in FIG. 25 to FIG. 27, one end of the first connecting portion 127 is in contact with a surface of one electrode portion 130 and the other end of the first connecting portion 127 is in contact with a surface of another electrode portion 130 adjacent to the one electrode portion 130, the surfaces facing the substrate 101. The second connecting portion 133 is a film formed simultaneously with the electrode portions 130 at the same process. The second connecting portion 133 is integral with the electrode portions 130. An insulating film 135 is provided between the second connecting portion 133 and the detection electrode Rx. With this structure, the detection electrodes Rx and the drive electrodes Tx are insulated from each other. The insulating film 135 is a resin insulating film, for example.

The following describes a method for manufacturing the fingerprint sensor illustrated in FIG. 27 in order of process. FIG. 28 to FIG. 31 are sectional views each illustrating a method for manufacturing the fingerprint sensor according to the second embodiment. The method for manufacturing the finger sensor according to the second embodiment is identical to that of the finger sensor according to the first embodiment (refer to FIG. 15 to FIG. 17) until the process by which the manufacturing apparatus (not illustrated) forms the source electrode 123, the drain electrode 125, and the connecting portion 127 in FIG. 28.

Figure 29:
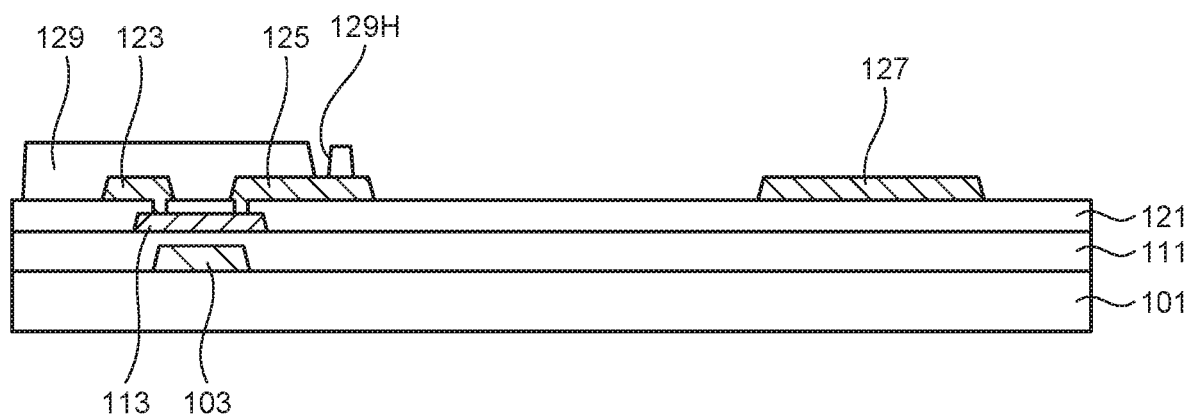
FIG. 29 is a sectional view illustrating the method for manufacturing the fingerprint sensor according to the second embodiment.

After forming the source electrode 123, the drain electrode 125, and the connecting portion 127, the manufacturing apparatus forms the insulating layer 129 only in the frame region GA, as illustrated in FIG. 29. The manufacturing apparatus forms the contact hole 129H in the insulating layer 129. The manufacturing apparatus forms an insulating film (not illustrated) above the substrate 101, for example. The insulating film covers the source electrode 123, the drain electrode 125, and the connecting portions 127. Subsequently, the manufacturing apparatus performs exposure processing on the insulating film. With this operation, part of the insulating film positioned in the fingerprint detection region FA and part of the insulating film in which the contact hole 129H is formed are exposed. Subsequently, the manufacturing apparatus performs developing processing on the insulating film to remove the exposed part. With this operation, the manufacturing apparatus forms the insulating layer 129 in the frame region GA and forms the contact hole 129H in the insulating layer 129.

Figure 30:
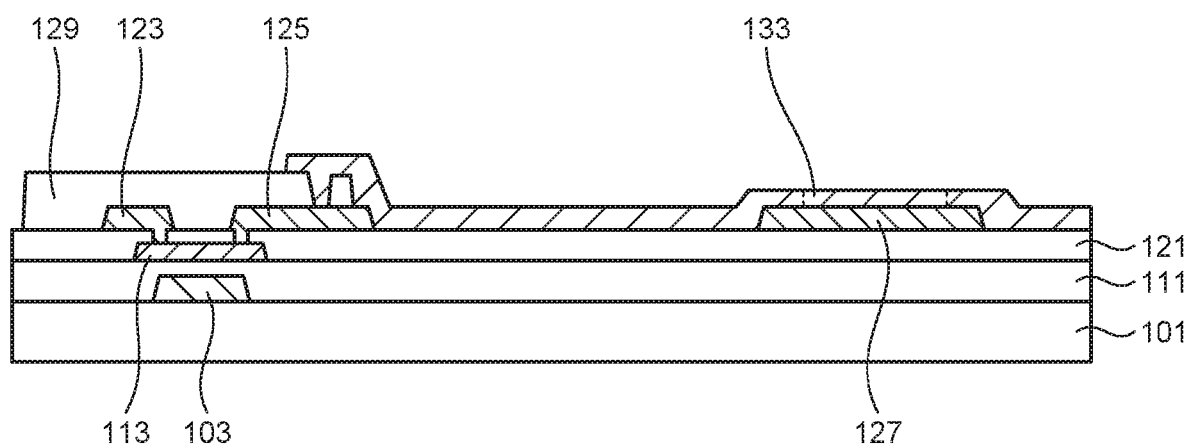
FIG. 30 is a sectional view illustrating the method for manufacturing the fingerprint sensor according to the second embodiment.

Subsequently, as illustrated in FIG. 30, the manufacturing apparatus forms a conductive film such as ITO (not illustrated) above the substrate 101. The conductive film is formed by the sputtering, for example. Subsequently, the manufacturing apparatus patterns the conductive film by the photolithography technique and the dry etching technique. With this operation, as illustrated in FIG. 31, the manufacturing apparatus forms the electrode portion 130 and the second connecting portions 133 out of the conductive film.

Figure 31:
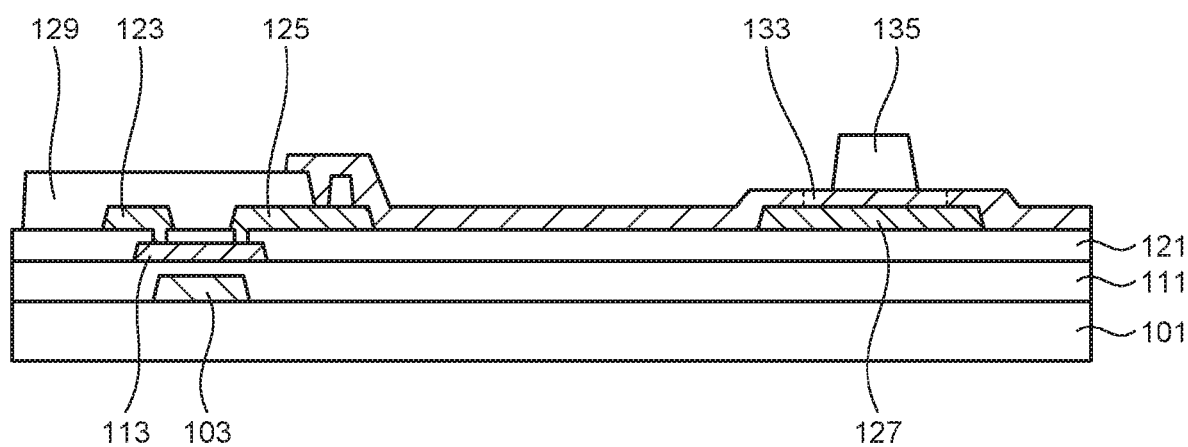
FIG. 31 is a sectional view illustrating the method for manufacturing the fingerprint sensor according to the second embodiment.

Subsequently, the manufacturing apparatus forms the insulating film 135 only in the fingerprint detection region FA, as illustrated in FIG. 31. The manufacturing apparatus forms an insulating film (not illustrate) above the substrate 101, for example. The insulating film covers the electrode portion 130 and the like. Subsequently, the manufacturing apparatus performs exposure processing on the insulating film. With this operation, the insulating film other than part thereof positioned on the second connecting portion 133 is exposed. Subsequently, the manufacturing apparatus performs developing process on the insulating film to remove the exposed part. With this operation, the manufacturing apparatus forms the insulating layer 129 on the second connecting portion 133.

The subsequent processes are the same as those of the first embodiment. As illustrated in FIG. 27, the manufacturing apparatus forms the detection electrode Rx including the first metallic layer 141, the second metallic layer 142, and the third metallic layer 143 on the insulating layer 129. The manufacturing apparatus forms the insulating film 150 (refer to FIG. 27) above the substrate 101. The insulating film 150 is formed by the CVD or the like. Through the foregoing processes, the fingerprint sensor 10A illustrated in FIG. 27 is completed.

Also in the fingerprint sensor 10A according to the second embodiment, the detection electrode Rx has the first metallic layer 141 and the second metallic layer 142. The first metallic layer 141 has a reflectance of visible light lower than that of the second metallic layer 142. With this structure, the fingerprint sensor 10A can reduce the reflection of light by the detection electrodes Rx and can reduce the occurrence of unintended patterns (e.g., moire and a light reflecting pattern) due to this reflection. Further, the structure can reduce the size of the connecting portions 127, and reduce the area covered with the connecting portions 127. With this structure, the fingerprint sensor 10A can further increase aperture of the fingerprint detection region FA and further increase the translucency of the fingerprint detection region FA.

Third Embodiment

Figure 32:
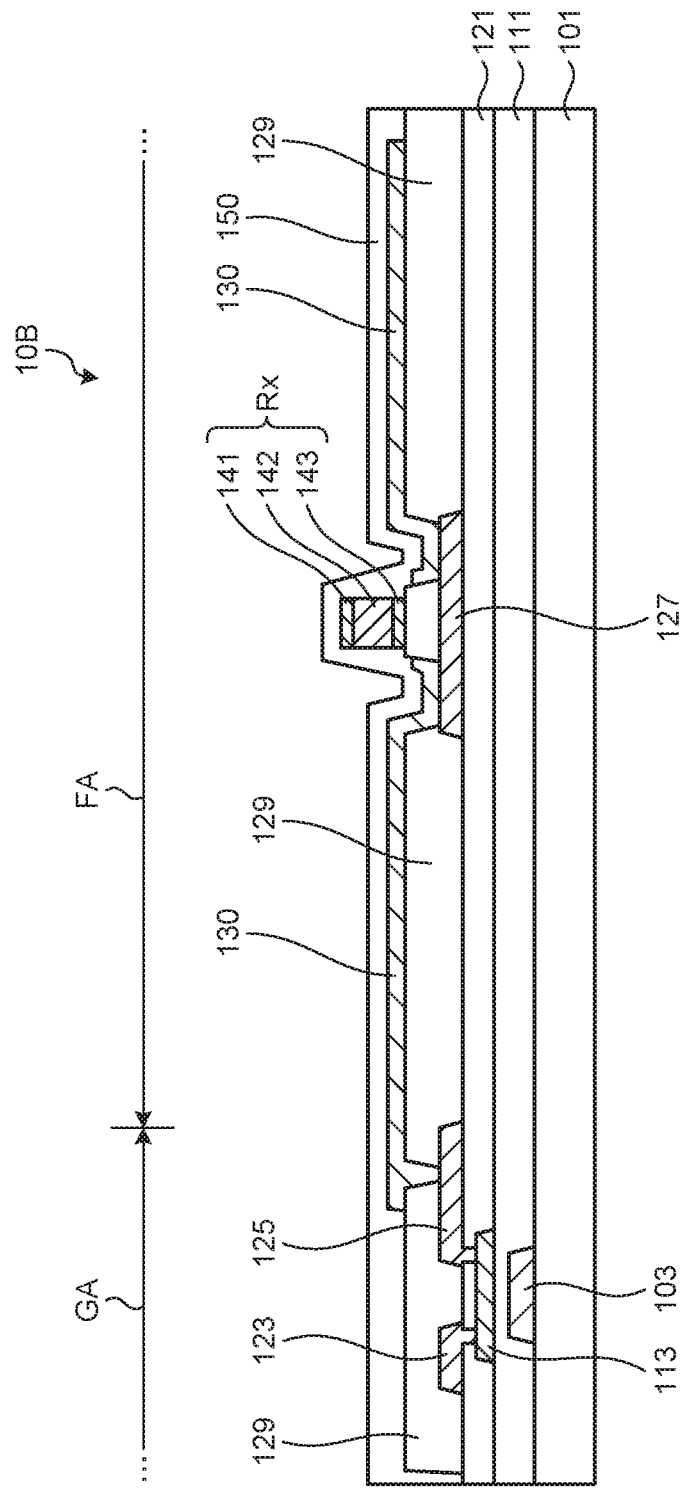
FIG. 32 is a sectional view illustrating a configuration example of a fingerprint sensor according to a third embodiment.

FIG. 32 is a sectional view illustrating a configuration example of a fingerprint sensor according to a third embodiment. As illustrated in FIG. 32, in the fingerprint sensor 10B according to the third embodiment, the insulating layer 129 is arranged between the substrate 101 and the electrode portion 130 in the fingerprint detection region FA. The insulating layer 129 is arranged on the second inter-layer insulating film 121, and the electrode portion 130 is arranged on the insulating layer 129, for example.

The process of arranging the insulating layer 129 on the substrate 101 in the fingerprint detection region FA may be performed by masking a region excluding the insulating layer 129 so as not to cause light incident on the region in the exposure processing for the insulating layer 129 described with reference to FIG. 29. With this operation, the insulating layer 129 is arranged on the substrate 101.

Also in the fingerprint sensor 10B according to the third embodiment, the detection electrode Rx has the first metallic layer 141 and the second metallic layer 142. The first metallic layer 141 has a reflectance of visible light lower than that of the second metallic layer 142. With this structure, the fingerprint sensor 10B can reduce the reflection of light by the detection electrodes Rx and can reduce the occurrence of unintended patterns due to the reflection.

The provision of the insulating layer 129 also in the display region AA that matches or substantially matches the fingerprint detection region FA flattens the display surface of the display region AA. In addition, the process of removing the first insulating film 129A described above (refer to FIG. 14) is eliminated, and the number of processes of manufacturing the fingerprint sensor 10B can be reduced in comparison with that of the fingerprint sensor 10A (refer to FIG. 14).

Fourth Embodiment

Figure 33:
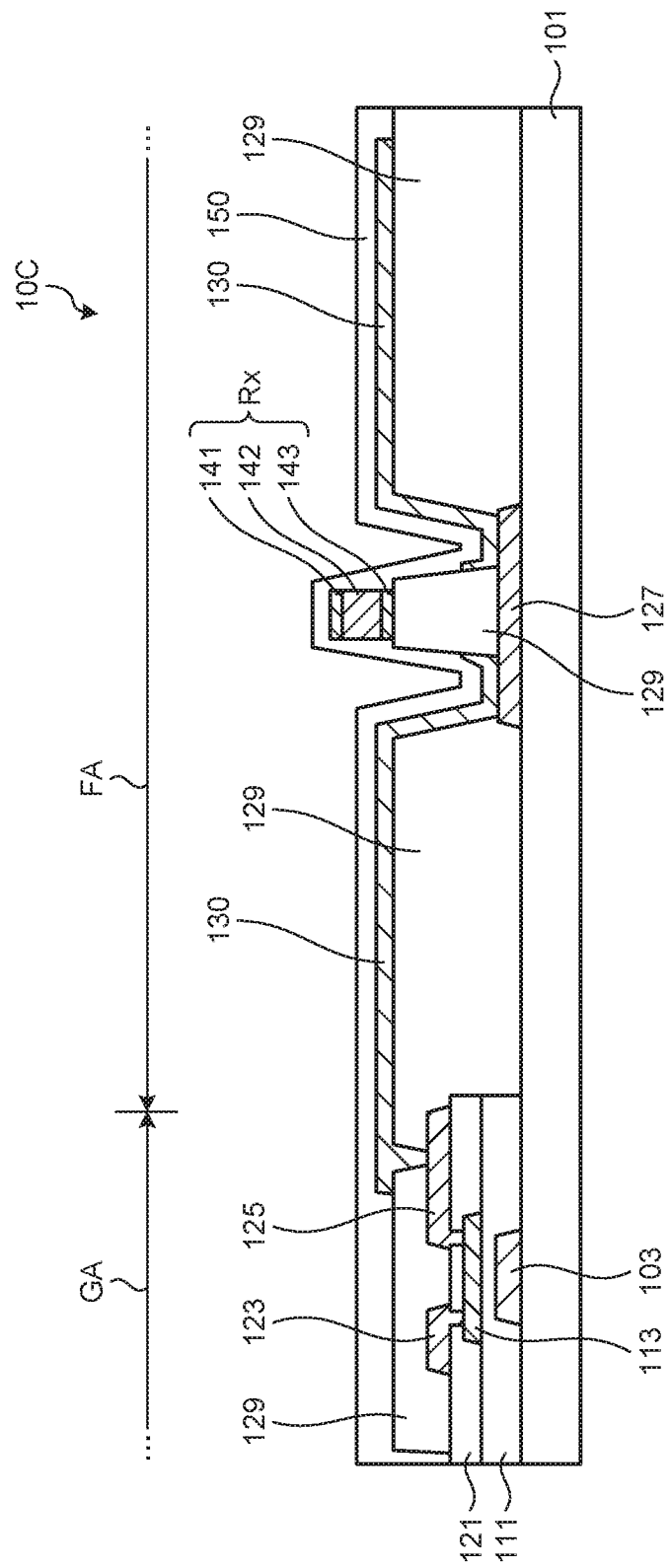
FIG. 33 is a sectional view illustrating a configuration example of a fingerprint sensor according to a fourth embodiment.

FIG. 33 is a sectional view illustrating a configuration example of a fingerprint sensor according to a fourth embodiment. As illustrated in FIG. 33, in this fingerprint sensor 10C according to the fourth embodiment, the first inter-layer insulating film 111 and the second inter-layer insulating film 121 are not arranged between the substrate 101 and the electrode portion 130. In the fingerprint detection region FA, the insulating layer 129 is arranged on the substrate 101, and the electrode portion 130 is arranged on the insulating layer 129.

Figure 16:
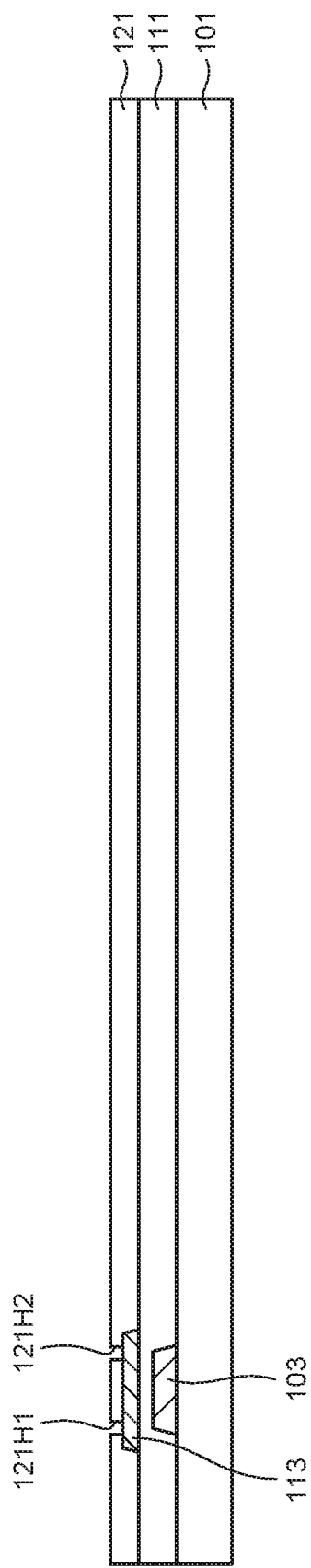
FIG. 16 is a sectional view illustrating the method for manufacturing the fingerprint sensor according to the first embodiment.

The process of removing the first inter-layer insulating film 111 and the second inter-layer insulating film 121 from the fingerprint detection region FA may be performed before or after the process of forming the contact holes 121H1 and 121H2 described with reference to FIG. 16. Before or after the contact holes 121H1 and 121H2 are formed, a manufacturing apparatus (not illustrated) may sequentially remove the second inter-layer insulating film 121 and the first inter-layer insulating film 111 of the fingerprint detection region FA by the photolithography technique and wet etching technique, for example.

Also in the fingerprint sensor 10C according to the fourth embodiment, the detection electrode Rx has the first metallic layer 141 and the second metallic layer 142. The first metallic layer 141 has a reflectance of visible light lower than that of the second metallic layer 142. With this structure, the fingerprint sensor 10C can reduce the reflection of light by the detection electrodes Rx and can reduce the occurrence of unintended patterns (e.g., moire and a light reflecting pattern) due to the reflection. In the fingerprint detection region FA, the first inter-layer insulating film 111 and the second inter-layer insulating film 121 are not arranged. With this structure, the fingerprint sensor 10C can reduce the reflection of light also at the position of the electrode portion 130 of the fingerprint detection region FA.

When a silicon nitride film is used for the first inter-layer insulating film 111 and the second inter-layer insulating film 121, the reflected light of light coming from the electrode portion 130 side is colored (e.g., the reflected light has a tinge of red). For this reason, the first inter-layer insulating film 111 and the second inter-layer insulating film 121 are not preferably arranged in the display region AA that matches or substantially matches the fingerprint detection region FA. This structure can prevent the reflected light from unintentionally having a tinge of red, which can improve coloring of the reflected light. Consequently, the quality of an image displayed on the display region AA can be improved.

Fifth Embodiment

Figure 34:
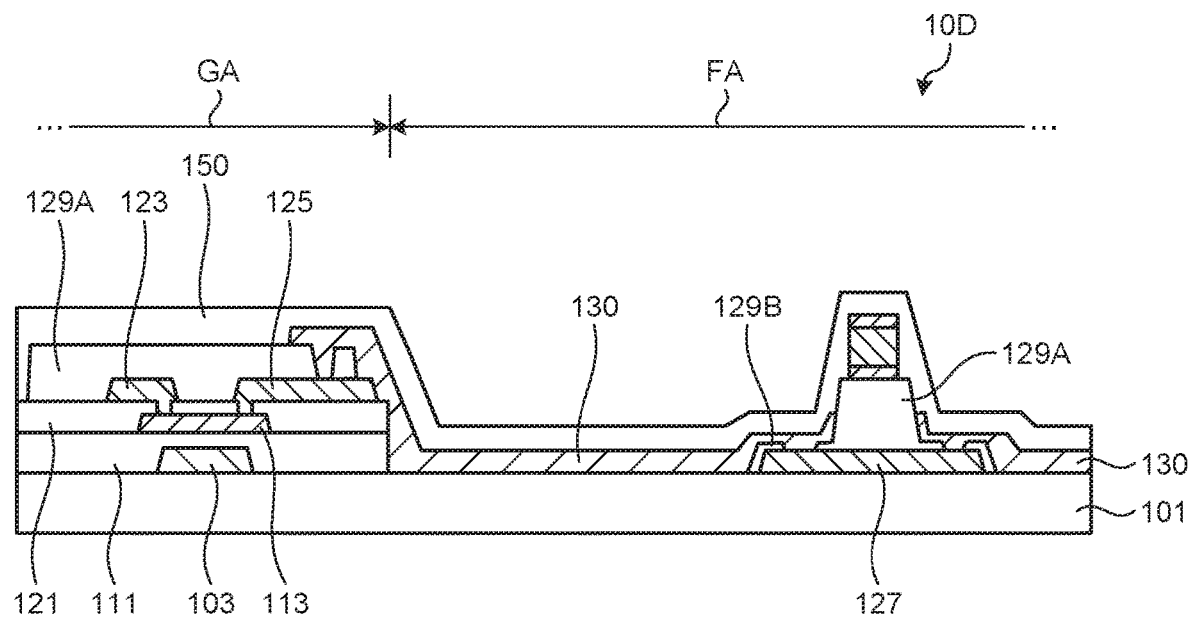
FIG. 34 is a sectional view illustrating a configuration example of a fingerprint sensor according to a fifth embodiment.

FIG. 34 is a sectional view illustrating a configuration example of a fingerprint sensor according to a fifth embodiment. As illustrated in FIG. 34, in this fingerprint sensor 10D according to the fourth embodiment, the first inter-layer insulating film 111 and the second inter-layer insulating film 121 are not arranged between the substrate 101 and the electrode portion 130. The insulating layer 129 (refer to FIG. 33) is not arranged between the substrate 101 and the electrode portion 130, either. In the fingerprint detection region FA, the electrode portion 130 is arranged on the substrate 101, and the electrode portion 130 is in contact with the substrate 101. The connecting portion 127 is arranged on the substrate 101, and the connecting portion 127 is in contact with the substrate 101.

In the fingerprint sensor 10D according to the fifth embodiment as well, the detection electrodes Rx have the first metallic layer 141 and the second metallic layer 142. The first metallic layer 141 has a reflectance of visible light lower than that of the second metallic layer 142. With this structure, the fingerprint sensor 10D can reduce the reflection of light by the detection electrodes Rx and can reduce the occurrence of unintended patterns due to the reflection. In the fingerprint detection region FA, the first inter-layer insulating film 111 and the second inter-layer insulating film 121 are not arranged. With this structure, the fingerprint sensor 10D can also reduce the reflection of light at the position of the electrode portion 130 of the fingerprint detection region FA. The insulating layer 129 (refer to FIG. 33) is not arranged at the position of the electrode portion 130, either. With this structure, the fingerprint sensor 10D can increase the translucency of the position of the electrode portion 130.

Figure 35:
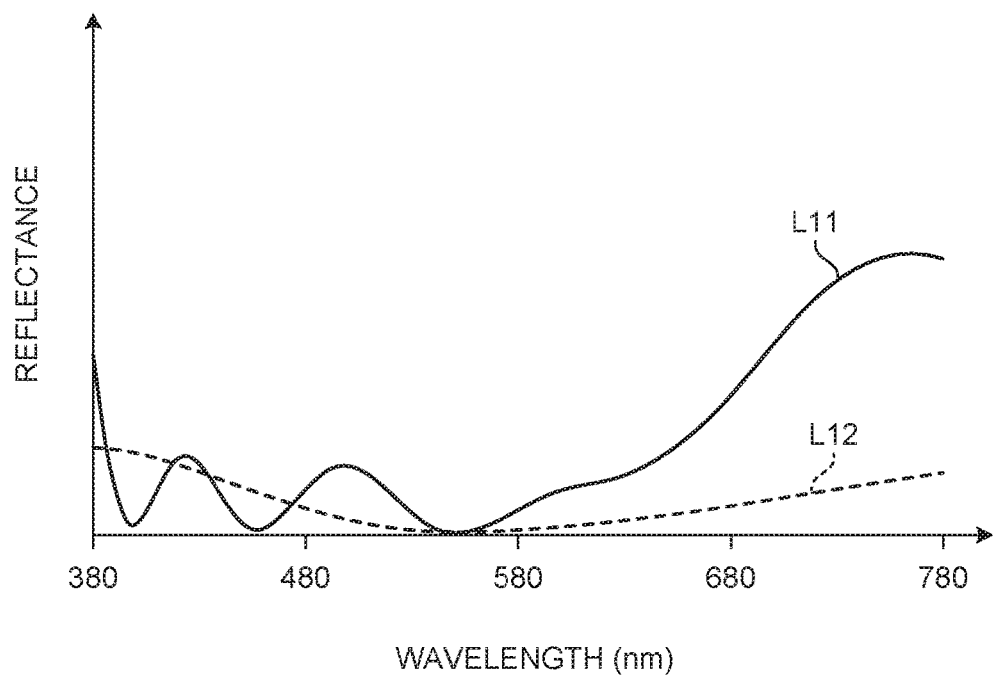
FIG. 35 is a diagram illustrating a relation between the wavelength of light incident on an electrode portion of a drive electrode and the reflectance of light.

FIG. 35 is a diagram illustrating a relation between the wavelength of light incident on the electrode portion of the drive electrode and the reflectance of light. The horizontal axis of FIG. 35 indicates the wavelength (nm) of light incident on the electrode portion 130, where 380 nm to 780 nm correspond to a wavelength range of visible light. The vertical axis of FIG. 35 indicates the reflectance of light coming from the electrode portion 130. In FIG. 35, L11 is measured data of the fingerprint sensor 10D. L12 is measured data of a fingerprint sensor in which a silicon nitride film is arranged between the substrate 101 and the electrode portion 130. As illustrated in FIG. 35, in the wavelength range of visible light, especially in the red wavelength range (e.g., 620 nm to 780 nm), L11 is lower in reflectance than L12. As illustrated in FIG. 35, the fingerprint sensor 10D can reduce the reflection of reddish light in particular, and can thus improve coloring of reflected light.

Sixth Embodiment

Figure 36:
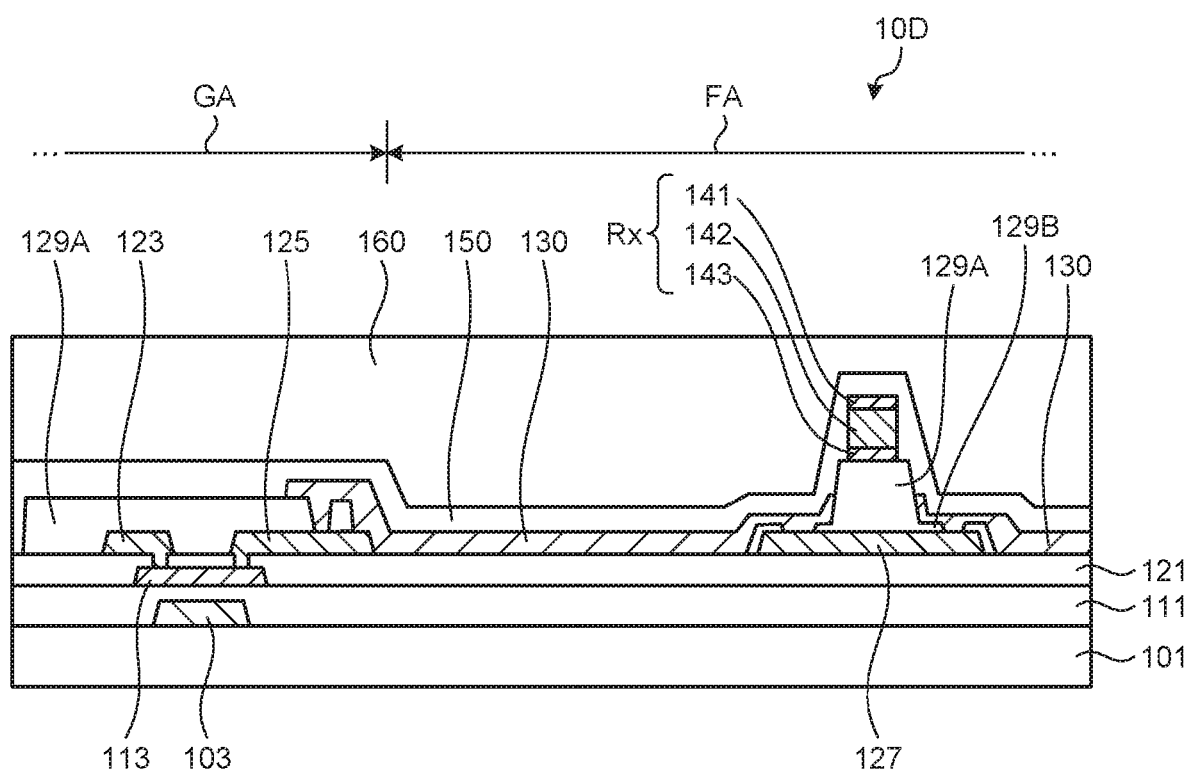
FIG. 36 is a sectional view illustrating a configuration example of a fingerprint sensor according to a sixth embodiment.

FIG. 36 is a sectional view illustrating a configuration example of a fingerprint sensor according to a sixth embodiment. As illustrated in FIG. 36, an insulating film 160 may be provided on the insulating film 150 in FIG. 35. The insulating film 160 is a resin film, for example, and is formed by the spin coating technique or printing. With the configuration illustrated in FIG. 36, the detection surface of a fingerprint sensor 10E including the drive electrodes Tx and the detection electrodes Rx is protected by the insulating film 160. Consequently, the fingerprint detection device 100 can improve reliability.

Seventh Embodiment

Figure 37:
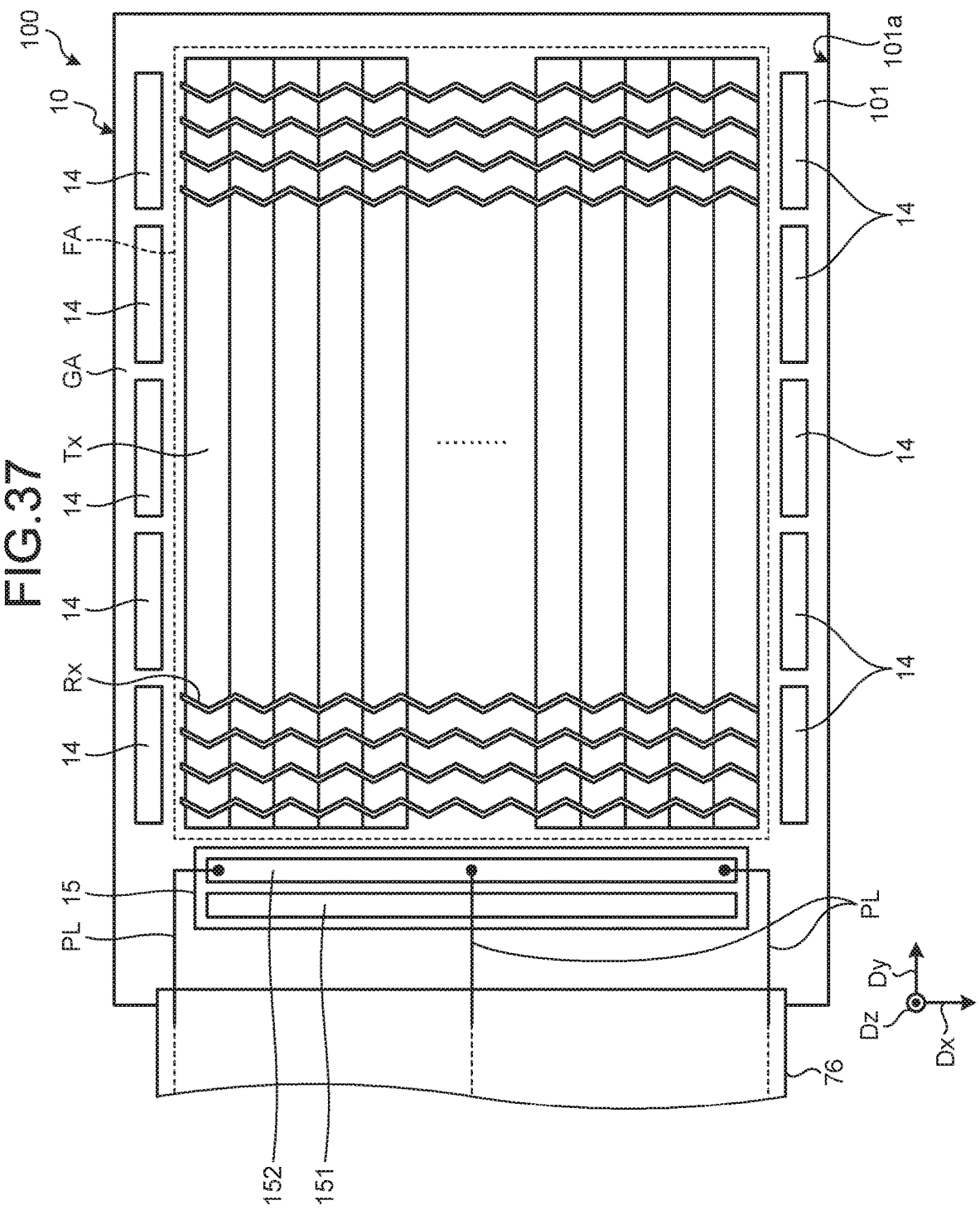
FIG. 37 is a block diagram illustrating a configuration example of the fingerprint detection device according to a seventh embodiment.
Figure 38:
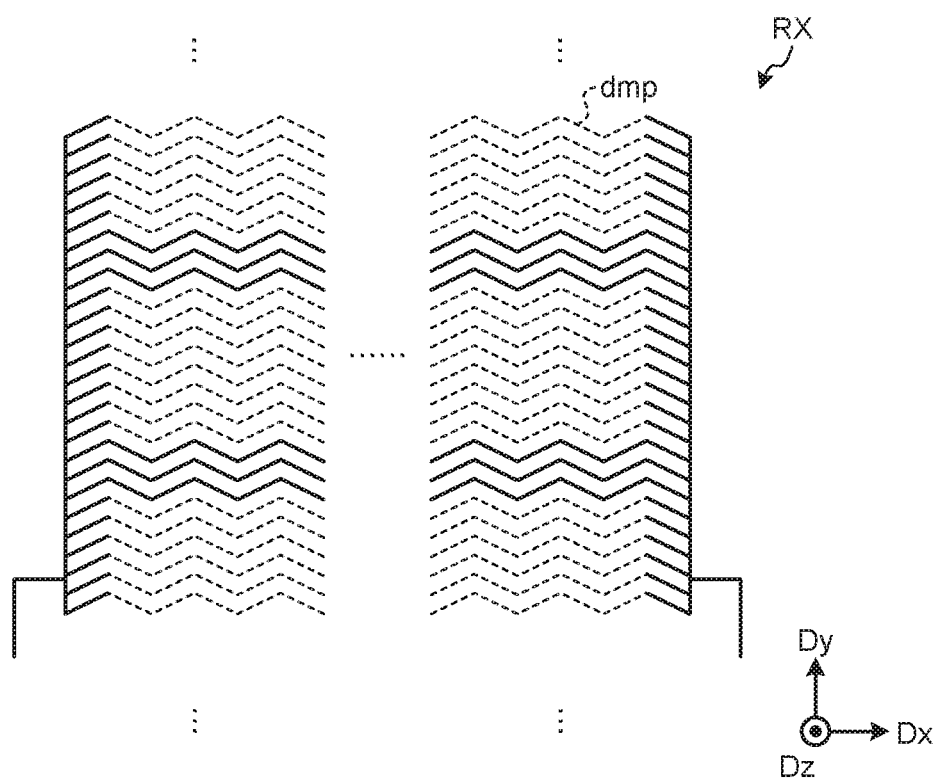
FIG. 38 is a plan view illustrating a configuration example of the detection electrodes according to the seventh embodiment.
Figure 39:
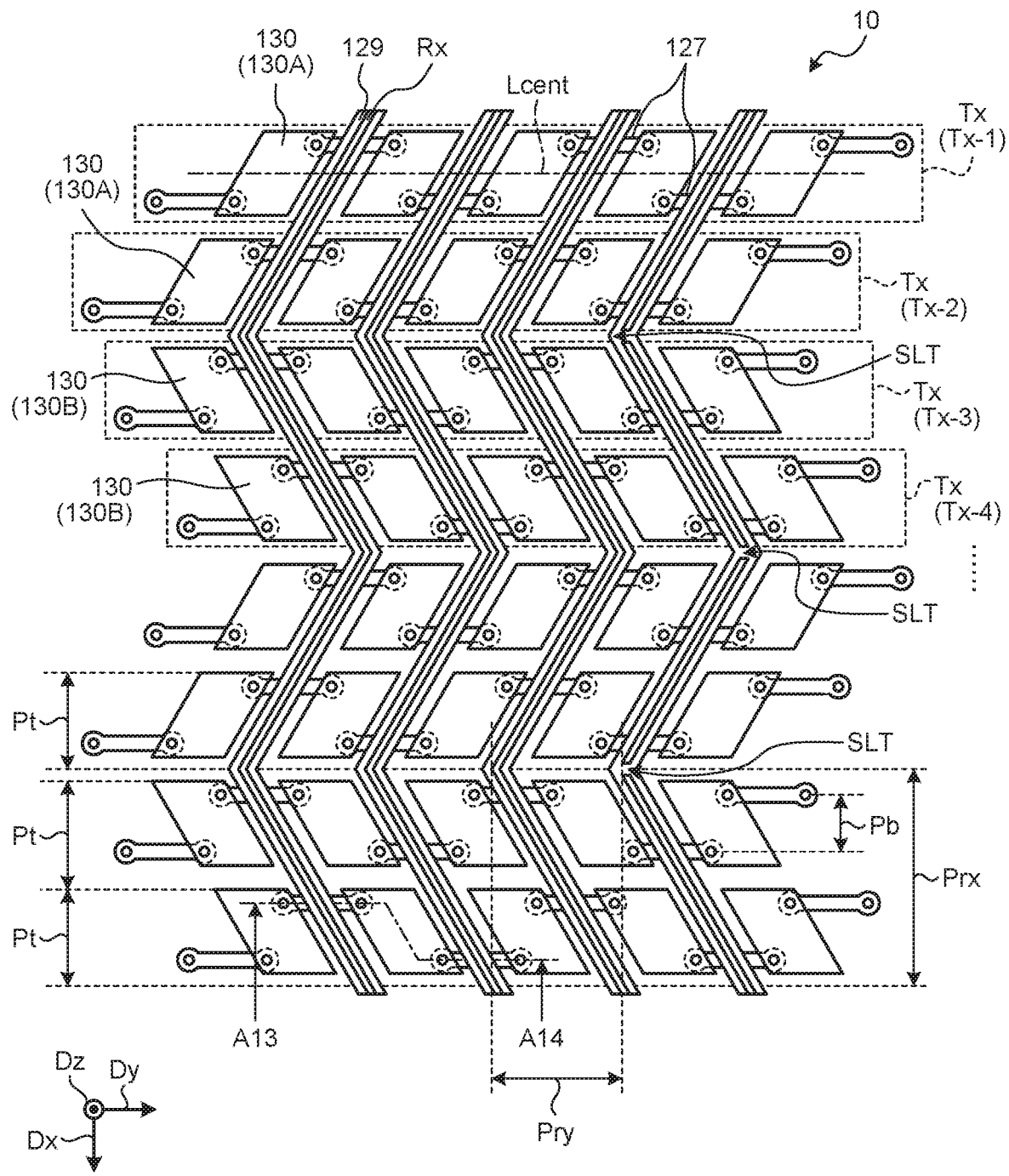
FIG. 39 is a plan view illustrating a configuration example of the detection electrodes according to the seventh embodiment.

FIG. 37 is a block diagram illustrating a configuration example of the fingerprint detection device according to a seventh embodiment. FIG. 38 is a plan view illustrating a configuration example of the detection electrodes according to the seventh embodiment. FIG. 39 is a plan view illustrating a configuration example of the detection electrodes according to the seventh embodiment. FIG. 39 is a partially enlarged view illustrating FIG. 38. In the seventh embodiment, the drive electrode driver 15 and the drive electrodes Tx are arranged in the second direction Dy in which the drive electrodes Tx extend. A plurality of detection electrode selection circuits 14 are arranged in the first direction Dx so as to sandwich the drive electrodes Tx therebetween.

The drive electrode driver 15 includes a shift register circuit 151 and a buffer circuit 152. The shift register circuit 151 sequentially selects the drive electrodes Tx in a time division manner. The buffer circuit 152 amplifies the drive signal Vs and supplies it to a selected drive electrode Tx. A plurality of power supply lines PL supply power to the buffer circuit 152 from the outside. The power supply lines PL supply power to both ends of the buffer circuit 152 and the central part thereof in the second direction Dy, for example.

With this operation, without supplying power from the upper side, power can be directly supplied to the buffer circuit 152 from the outside of the drive electrode driver 15, and a load during power supply is reduced.

As illustrated in FIG. 38, dummy electrodes dmp are arranged such that conductive materials such as metal discontinue and not continuous in the first direction. As illustrated in FIG. 39, slits SLT separate the conductive materials. This structure makes the detection electrodes Rx less noticeable and invisible.

While exemplary embodiments have been described, the embodiments are not intended to limit the present disclosure. The contents disclosed in the embodiments are given by way of example only, and various modifications may be made without departing from the spirit of the present disclosure. Although a transmissive liquid crystal display device capable of color display has been described as the display device 1 in the first embodiment, for example, the present disclosure is not limited to a transmissive liquid crystal display device supporting color display and may be a transmissive liquid crystal display device for monochrome display. Appropriate modifications made without departing from the gist of the present disclosure also naturally belong to the technical scope of the present disclosure.

The fingerprint detection device and the display device of the preset disclosure include the following aspects:

(1) A fingerprint detection device, comprising:
a substrate;
a plurality of drive electrodes provided on one surface side of the substrate and arranged in a first direction;
a plurality of detection electrodes provided on the one surface side and arranged in a second direction intersecting the first direction; and
an insulating layer provided in a normal direction of the substrate between each of the drive electrodes and the corresponding detection electrodes, wherein
the detection electrodes intersect the drive electrodes in the normal direction of the substrate,
each of the detection electrodes includes:
a first metallic layer; and
a second metallic layer positioned closer to the one surface than the first metallic layer to the one surface, and
the first metallic layer has a reflectance of visible light lower than that of the second metallic layer.

(2) The fingerprint detection device according to (1), further comprising an insulating film provided on the one surface to cover the detection electrodes, wherein
the insulating film includes at least one of a silicon nitride film or a light-shielding resin film.

(3) The fingerprint detection device according to (1) or (2), wherein each of the drive electrodes includes:
a plurality of electrode portions arranged spaced apart from each other in a plan view; and
a plurality of connecting portions each connecting adjacent electrode portions of the electrode portions to each other,
the electrode portions are translucent electrodes, and
the detection electrodes are metallic thin lines.

(4) The fingerprint detection device according to (3), wherein
the insulating layer further includes:
a first insulating film arranged between the connecting portions and the corresponding detection electrodes in the normal direction of the substrate; and
a second insulating film arranged between the connecting portions and the corresponding detection electrodes, and the second insulating film is thinner than the first insulating film.

(5) The fingerprint detection device according to (4), wherein each of the electrode portions includes:
an electrode main body; and
a protruding portion in a plan view protruding from the electrode main body toward an electrode portion adjacent to the corresponding electrode portion, and
the second insulating film is arranged between the corresponding electrode portion and the protruding portion.

(6) The fingerprint detection device according to any one of (1) to (5), further comprising an inter-layer insulating film provided on the one surface side of the substrate, wherein
the inter-layer insulating film is arranged between the substrate and the drive electrodes, and
a sum of a thickness of the inter-layer insulating film and a thickness of the drive electrodes is 150 nm or less.

(7) The fingerprint detection device according to any one of (1) to (6), further comprising an inter-layer insulating film provided on the one surface of the substrate, wherein
the substrate includes:
a fingerprint detection region in which the drive electrodes and the detection electrodes are arranged; and
a frame region adjacent to the fingerprint detection region, and
the inter-layer insulating film is arranged in the frame region and is not arranged in the fingerprint detection region.

(8) The fingerprint detection device according to any one of (1) to (6), further comprising an inter-layer insulating film provided on the one surface of the substrate, wherein
the substrate includes:
a fingerprint detection region in which the drive electrodes and the detection electrodes are arranged; and
a frame region adjacent to the fingerprint detection region,
the inter-layer insulating film is arranged in the frame region on the substrate, and
the drive electrodes are arranged in the fingerprint detection region on the substrate.

(9) A display device comprising:
a display panel; and
a fingerprint detection device arranged facing the display panel, the finger print detection device comprising:
a substrate;
a plurality of drive electrodes provided on one surface side of the substrate and arranged in a first direction;
a plurality of detection electrodes provided on the one surface side and arranged in a second direction intersecting the first direction; and
an insulating layer provided in a normal direction of the substrate between each of the drive electrodes and the corresponding detection electrodes, wherein
the detection electrodes intersect the drive electrodes in the normal direction of the substrate,
each of the detection electrodes includes:
a first metallic layer; and
a second metallic layer positioned closer to the one surface than the first metallic layer to the one surface, and
the first metallic layer has a reflectance of visible light lower than that of the second metallic layer.

What is claimed is:
1. A fingerprint detection device, comprising:
a substrate;
a plurality of drive electrodes provided on one surface side of the substrate and arranged in a first direction;
a plurality of detection electrodes provided on the one surface side and arranged in a second direction intersecting the first direction; and
an insulating layer provided in a normal direction of the substrate between each of the drive electrodes and the corresponding detection electrodes, wherein
the detection electrodes intersect the drive electrodes in the normal direction of the substrate,
each of the detection electrodes includes:
a first metallic layer; and
a second metallic layer positioned closer to the one surface than the first metallic layer to the one surface, and
the first metallic layer has a reflectance of visible light lower than that of the second metallic layer.

2. The fingerprint detection device according to claim 1, further comprising an insulating film provided on the one surface to cover the detection electrodes, wherein
the insulating film includes at least one of a silicon nitride film or a light-shielding resin film.

3. The fingerprint detection device according to claim 1, wherein
each of the drive electrodes includes:
a plurality of electrode portions arranged spaced apart from each other in a plan view; and
a plurality of connecting portions each connecting adjacent electrode portions of the electrode portions to each other,
the electrode portions are translucent electrodes, and
the detection electrodes are metallic thin lines.

4. The fingerprint detection device according to claim 3, wherein
the insulating layer further includes:
a first insulating film arranged between the connecting portions and the corresponding detection electrodes in the normal direction of the substrate; and
a second insulating film arranged between the connecting portions and the corresponding detection electrodes, and
the second insulating film is thinner than the first insulating film.

5. The fingerprint detection device according to claim 4, wherein
each of the electrode portions includes:
an electrode main body; and
a protruding portion in a plan view protruding from the electrode main body toward an electrode portion adjacent to the corresponding electrode portion, and
the second insulating film is arranged between the corresponding electrode portion and the protruding portion.

6. The fingerprint detection device according to claim 1, further comprising an inter-layer insulating film provided on the one surface side of the substrate, wherein
the inter-layer insulating film is arranged between the substrate and the drive electrodes, and
a sum of a thickness of the inter-layer insulating film and a thickness of the drive electrodes is 150 nm or less.

7. The fingerprint detection device according to claim 1, further comprising an inter-layer insulating film provided on the one surface of the substrate, wherein
the substrate includes:
a fingerprint detection region in which the drive electrodes and the detection electrodes are arranged; and
a frame region adjacent to the fingerprint detection region, and
the inter-layer insulating film is arranged in the frame region and is not arranged in the fingerprint detection region.

8. The fingerprint detection device according to claim 1, further comprising an inter-layer insulating film provided on the one surface of the substrate, wherein
the substrate includes:
a fingerprint detection region in which the drive electrodes and the detection electrodes are arranged; and
a frame region adjacent to the fingerprint detection region,
the inter-layer insulating film is arranged in the frame region on the substrate, and
the drive electrodes are arranged in the fingerprint detection region on the substrate.

9. A display device comprising:
a display panel; and
a fingerprint detection device arranged facing the display panel, the finger print detection device comprising:
a substrate;
a plurality of drive electrodes provided on one surface side of the substrate and arranged in a first direction;
a plurality of detection electrodes provided on the one surface side and arranged in a second direction intersecting the first direction; and
an insulating layer provided in a normal direction of the substrate between each of the drive electrodes and the corresponding detection electrodes, wherein
the detection electrodes intersect the drive electrodes in the normal direction of the substrate,
each of the detection electrodes includes:
a first metallic layer; and
a second metallic layer positioned closer to the one surface than the first metallic layer to the one surface, and
the first metallic layer has a reflectance of visible light lower than that of the second metallic layer.

10. The display device according to claim 9, further comprising an insulating film provided on the one surface to cover the detection electrodes, wherein
the insulating film includes at least one of a silicon nitride film or a light-shielding resin film.

11. The display device according to claim 9, wherein
each of the drive electrodes includes:
a plurality of electrode portions arranged spaced apart from each other in a plan view; and
a plurality of connecting portions each connecting adjacent electrode portions of the electrode portions to each other,
the electrode portions are translucent electrodes, and
the detection electrodes are metallic thin lines.

12. The display device according to claim 11, wherein
the insulating layer further includes:
a first insulating film arranged between the connecting portions and the corresponding detection electrodes in the normal direction of the substrate; and
a second insulating film arranged between the connecting portions and the corresponding detection electrodes, and
the second insulating film is thinner than the first insulating film.

13. The display device according to claim 12, wherein
each of the electrode portions includes:
an electrode main body; and
a protruding portion in a plan view protruding from the electrode main body toward an electrode portion adjacent to the corresponding electrode portion, and
the second insulating film is arranged between the corresponding electrode portion and the protruding portion.

14. The display device according to claim 9, further comprising an inter-layer insulating film provided on the one surface side of the substrate, wherein
the inter-layer insulating film is arranged between the substrate and the drive electrodes, and
a sum of a thickness of the inter-layer insulating film and a thickness of the drive electrodes is 150 nm or less.

15. The display device according to claim 9, further comprising an inter-layer insulating film provided on the one surface of the substrate, wherein
the substrate includes:
a fingerprint detection region in which the drive electrodes and the detection electrodes are arranged; and
a frame region adjacent to the fingerprint detection region, and
the inter-layer insulating film is arranged in the frame region and is not arranged in the fingerprint detection region.

16. The display device according to claim 9, further comprising an inter-layer insulating film provided on the one surface of the substrate, wherein
the substrate includes:
a fingerprint detection region in which the drive electrodes and the detection electrodes are arranged; and
a frame region adjacent to the fingerprint detection region,
the inter-layer insulating film is arranged in the frame region on the substrate, and
the drive electrodes are arranged in the fingerprint detection region on the substrate.

* * * * *